US012702483B2

(12) United States Patent
Lynch

(10) Patent No.: US 12,702,483 B2
(45) Date of Patent: Aug. 11, 2026

(54) CONFORMATION BASED BONE MODEL GENERATION AND ASSOCIATED SURGICAL TECHNIQUES

(71) Applicant: Albert C. Lynch, Landenberg, PA (US)

(72) Inventor: Albert C. Lynch, Landenberg, PA (US)

( * ) Notice: Subject to any disclaimer, the term of this patent is extended or adjusted under 35 U.S.C. 154(b) by 287 days.

(21) Appl. No.: 18/533,504

(22) Filed: Dec. 8, 2023

(65) Prior Publication Data

US 2024/0189034 A1 Jun. 13, 2024

Related U.S. Application Data

(60) Provisional application No. 63/431,093, filed on Dec. 8, 2022.

(51) Int. Cl.
*A61B 34/10* (2016.01)
*G06T 1/00* (2006.01)

(52) U.S. Cl.
CPC ............ *A61B 34/10* (2016.02); *G06T 1/0007* (2013.01); *A61B 2034/105* (2016.02); *G06T 2211/00* (2013.01)

(58) Field of Classification Search
CPC ...................................................... G06V 40/28
See application file for complete search history.

(56) References Cited

U.S. PATENT DOCUMENTS

2013/0211792 A1 8/2013 Kang et al.
2014/0236153 A1* 8/2014 Edelhauser ............ A61B 17/62 606/56
2014/0278322 A1* 9/2014 Jaramaz ................. G16H 50/20 703/11
2017/0020609 A1* 1/2017 Wentorf ................... A61B 6/03
2017/0258526 A1* 9/2017 Lang .................... A61B 17/157
(Continued)

FOREIGN PATENT DOCUMENTS

EP 2767252 B1 4/2019
JP 2023179239 A * 12/2023
(Continued)

OTHER PUBLICATIONS

M.M. Chaudhary, (2021). Role of the Ilizarov fixator in high tibial osteotomy. Journal of clinical orthopaedics and trauma, 25, 101724.
(Continued)

*Primary Examiner* — Di Xiao
(74) *Attorney, Agent, or Firm* — Daylight Law, P.C.

(57) ABSTRACT

Methods and systems related to bone model generation and associated surgical techniques are discussed herein. A disclosed method for generating a bone model for a patient bone includes storing a conforming bone template model, accepting a nonconformity of the patient bone, and generating a nonconforming bone model using the nonconformity of the patient bone and the bone template model. The nonconformity is used to set a constraint of the conforming bone template model to a value and the nonconforming bone model has the value for the constraint. The nonconforming bone model can be generated using a bone model generator engine. In specific embodiments, the nonconformity can be described and accepted for use by the bone model generator engine using values that can be obtained from standard planar radiographs.

21 Claims, 22 Drawing Sheets

(56) References Cited

U.S. PATENT DOCUMENTS

| | | | | |
|---|---|---|---|---|
| 2018/0263586 | A1* | 9/2018 | Henchie | G16H 50/30 |
| 2021/0192759 | A1 | 6/2021 | Lang | |
| 2021/0244477 | A1 | 8/2021 | Singh et al. | |
| 2023/0019873 | A1* | 1/2023 | Landon | G06T 19/20 |
| 2023/0087313 | A1* | 3/2023 | Metcalfe | A61B 17/8061 |

FOREIGN PATENT DOCUMENTS

| | | | | | |
|---|---|---|---|---|---|
| JP | 7537058 | B2 | * | 8/2024 | G06T 7/70 |
| UA | 74084 | C2 | * | 10/2005 | |
| WO | WO-2012130470 | A1 | * | 10/2012 | G06T 11/00 |

OTHER PUBLICATIONS

International Search Report and Written Opinion from International Application No. PCT/US23/83065 dated Mar. 20, 2024, 15 pages.

L. Modenese, et al. (2021). Dependency of lower limb joint reaction forces on femoral version. Gait & posture, 88, 318-321.

* cited by examiner

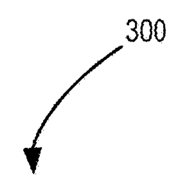

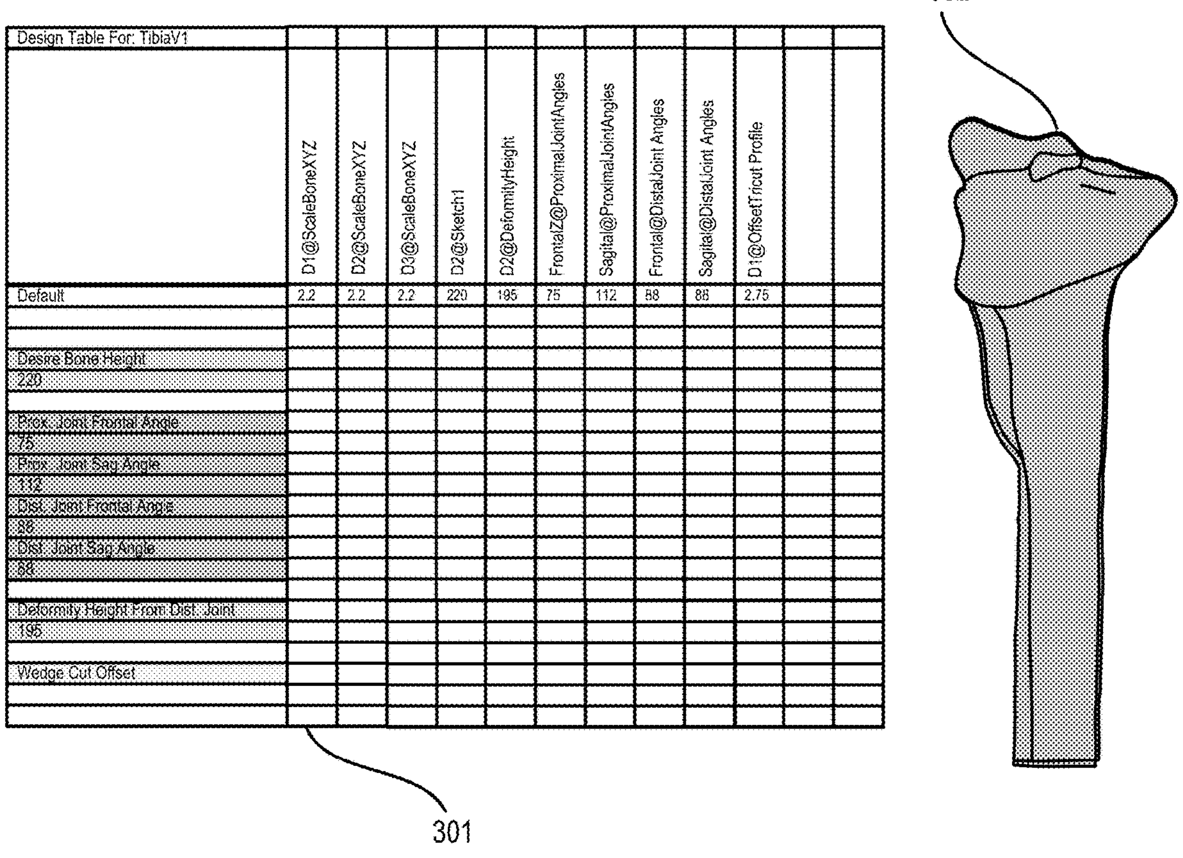

| Design Table For: TibiaV1 | | | | | | | | | | | | |
|---|---|---|---|---|---|---|---|---|---|---|---|---|
| | D1@ScaleBoneXYZ | D2@ScaleBoneXYZ | D3@ScaleBoneXYZ | D2@Sketch1 | D2@DeformityHeight | FrontalZ@ProximalJointAngles | Sagital@ProximalJointAngles | Frontal@DistalJoint Angles | Sagital@DistalJoint Angles | D1@OffsetTricut Profile | | |
| Default | 2.2 | 2.2 | 2.2 | 220 | 195 | 75 | 112 | 88 | 88 | 2.75 | | |
| | | | | | | | | | | | | |
| | | | | | | | | | | | | |
| Desire Bone Height | | | | | | | | | | | | |
| 220 | | | | | | | | | | | | |
| | | | | | | | | | | | | |
| Prox. Joint Frontal Angle | | | | | | | | | | | | |
| 75 | | | | | | | | | | | | |
| Prox. Joint Sag Angle | | | | | | | | | | | | |
| 112 | | | | | | | | | | | | |
| Dist. Joint Frontal Angle | | | | | | | | | | | | |
| 88 | | | | | | | | | | | | |
| Dist. Joint Sag Angle | | | | | | | | | | | | |
| 88 | | | | | | | | | | | | |
| | | | | | | | | | | | | |
| Deformity Height From Dist. Joint | | | | | | | | | | | | |
| 195 | | | | | | | | | | | | |
| | | | | | | | | | | | | |
| Wedge Cut Offset | | | | | | | | | | | | |
| | | | | | | | | | | | | |
| | | | | | | | | | | | | |

| A | B | C | D |
|---|---|---|---|
| Design Table For: TibiaV1 | SBX@ScaleBoneX | SBY@ScaleBoneY | SBZ@ScaleBoneZ |
| Default | 1.83 | 1.83 | 1.83 |
| Patient 1 | 1.83 | 1.83 | 1.83 |
| Patient 2 | 1.83 | 1.83 | 1.83 |
| Patient 3 | 1.83 | 1.83 | 1.83 |
| | | | |
| | | | |
| BONE DIMENSIONS | | Proximal Front | Proximal Sagital |
| Desire Bone Height | | 100mm Prox. F | 100mm Prox. Sa |
| 183 | | 20.83 | 22.02 |
| Scale Factor Frontal | | Scaled Prox. Fro | Scaled Prox. Sag |
| 1 | | 38.12 | 40.30 |
| Scale Factor Sagital | | Desired Prox. F | Desired Prox. Sa |
| 1 | | 50 | 42 |

420

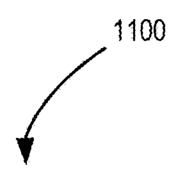
| 2 | | D1@ScaleBoneXYZ | D2@ScaleBoneXYZ |
|---|---|---|---|
| 3 | Default | 2 | 2 |
| 4 | | | |
| 5 | | | |
| 6 | Desired Bone Height | | |
| 7 | 200 | | |
| 8 | | | |
| 9 | Prox. Joint Frontal Angle | | |
| 10 | 113.5 | | |
| 11 | Prox. Joint Sag. Angle | | |
| 12 | 110 | | |
| 13 | | | |
| 14 | Dist. Joint Frontal Angle | | |
| 15 | 80.01 | | |
| 16 | Dist. Joint Sag. Angle | | |
| 17 | 88.5 | | |
| 18 | | | |
| 19 | Deformity Height From Dist. Joint | | |
| 20 | 170 | | |
| 21 | | | |
| 22 | Wedge Cut Offset | | |
| 23 | 2 | | |
| 24 | | | |
| 25 | | | |
| 26 | Torsion Magnitude | | |
| 27 | 40 | | |
| 28 | | | |
| 29 | | | |
| 30 | | | |
| 31 | | | |
| 32 | | | |
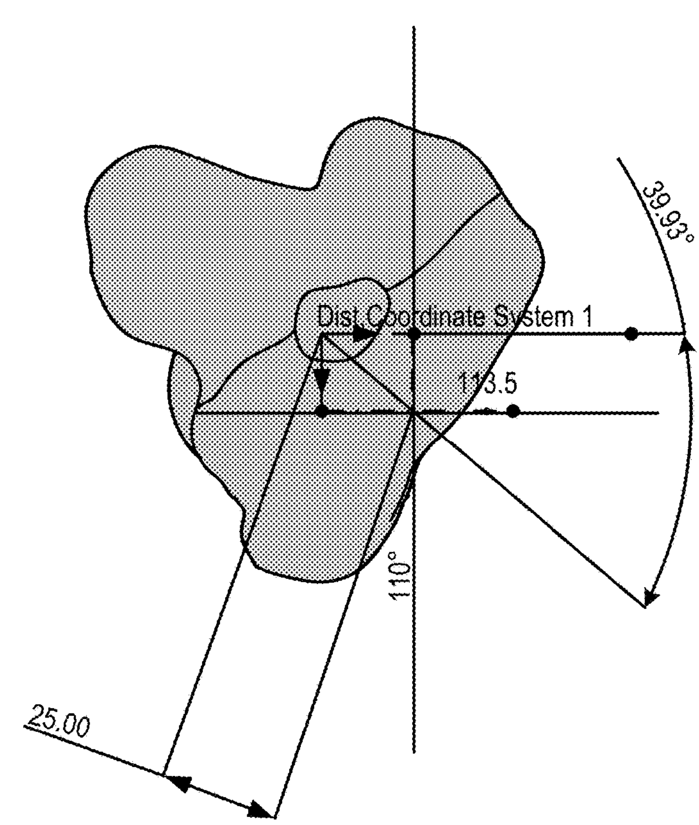
Fig. 11

| | A |
|---|---|
| 22 | Deformity Height From Prox. Joint [mm] |
| 23 | 30 |
| 24 | |
| 25 | Proximal Bisection Width [mm] |
| 26 | 7 |
| 27 | Distal Bisection Width [mm] |
| 28 | 7 |

| | A |
|---|---|
| 17 | Prox. Joint Sagittal Angle[deg.] |
| 18 | 100 |
| 19 | Prox. Joint Frontal Angle[deg.] |
| 20 | 65 |

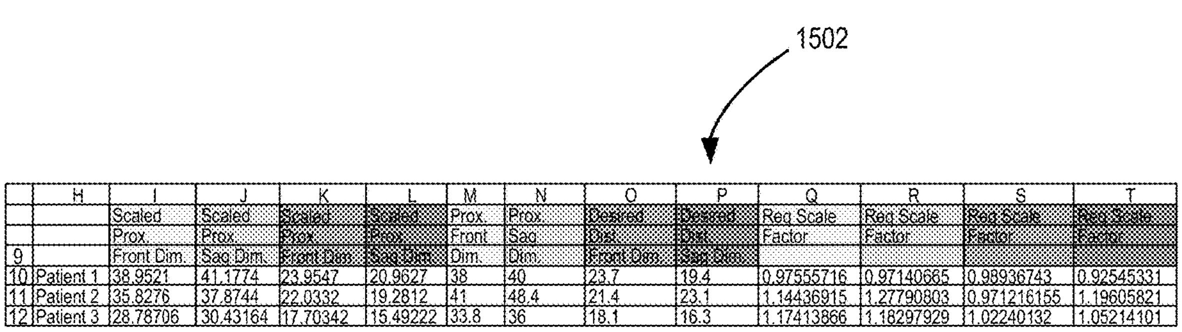
| | H | I | J | K | L | M | N | O | P | Q | R | S | T |
|---|---|---|---|---|---|---|---|---|---|---|---|---|---|
| | | Scaled | Scaled | Scaled | Scaled | Prox. | Prox. | Desired | Desired | Req Scale | Req Scale | Req Scale | Req Scale |
| | | Prox. | Prox. | Prox. | Prox. | Front | Sag | Dist. | Dist. | Factor | Factor | Factor | Factor |
| 9 | | Front Dim. | Sag Dim. | Front Dim. | Sag Dim. | Dim. | Dim. | Front Dim. | Sag Dim. | | | | |
| 10 | Patient 1 | 38.9521 | 41.1774 | 23.9547 | 20.9627 | 38 | 40 | 23.7 | 19.4 | 0.97555716 | 0.97140665 | 0.98936743 | 0.92545331 |
| 11 | Patient 2 | 35.8276 | 37.8744 | 22.0332 | 19.2812 | 41 | 48.4 | 21.4 | 23.1 | 1.14436915 | 1.27790803 | 0.971216155 | 1.19605821 |
| 12 | Patient 3 | 28.78706 | 30.43164 | 17.70342 | 15.49222 | 33.8 | 36 | 18.1 | 16.3 | 1.17413866 | 1.18297929 | 1.02240132 | 1.05214101 |
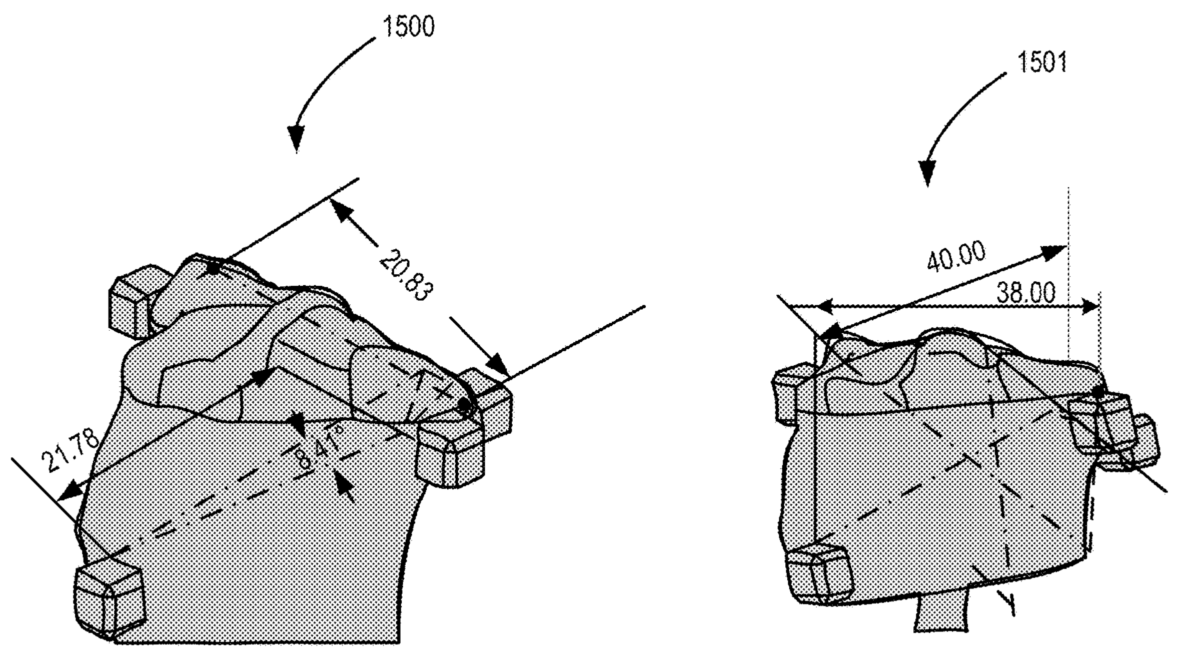
FIG.15

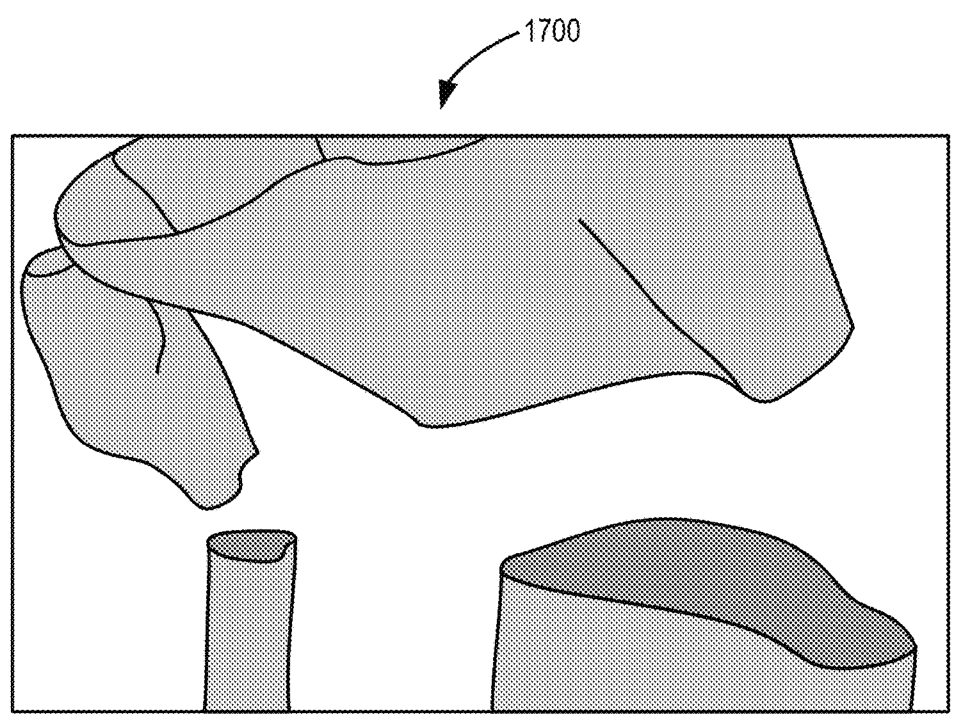
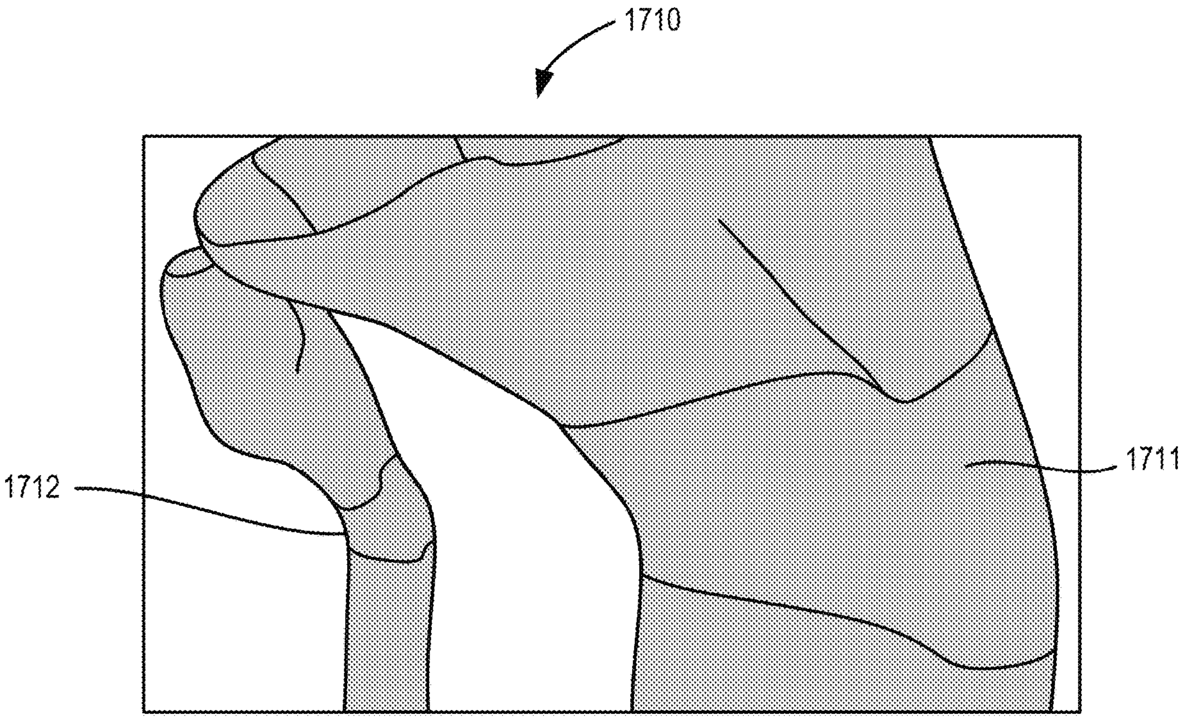
FIG. 17

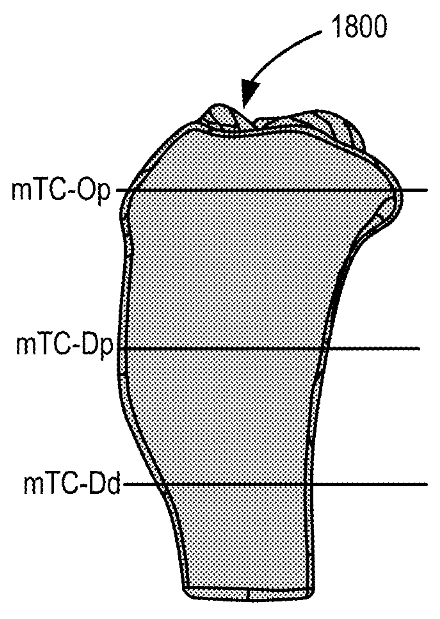
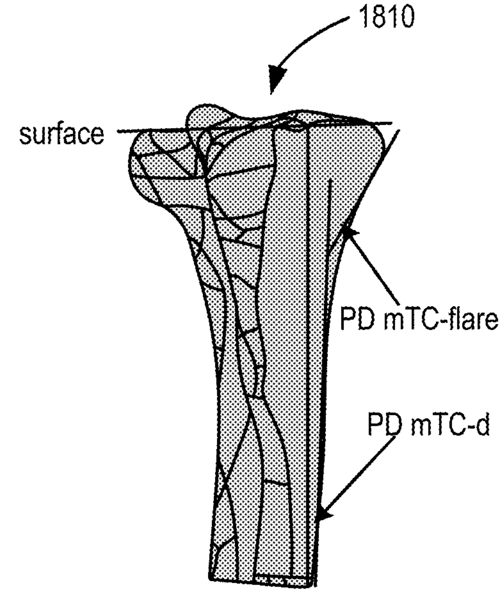
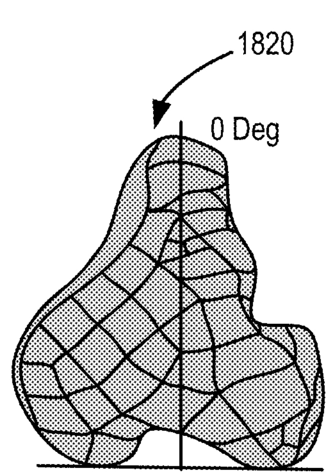
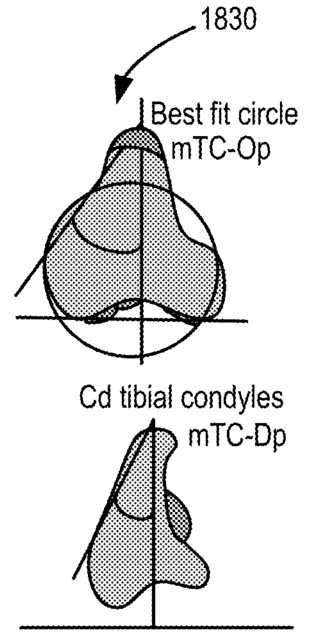
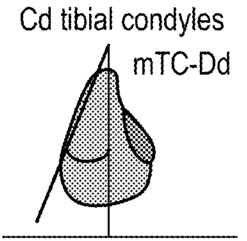
FIG.18

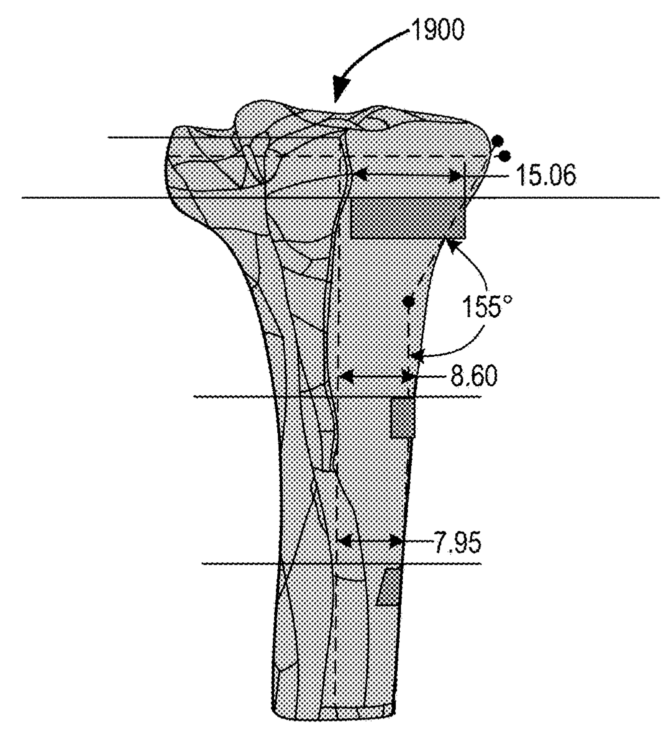
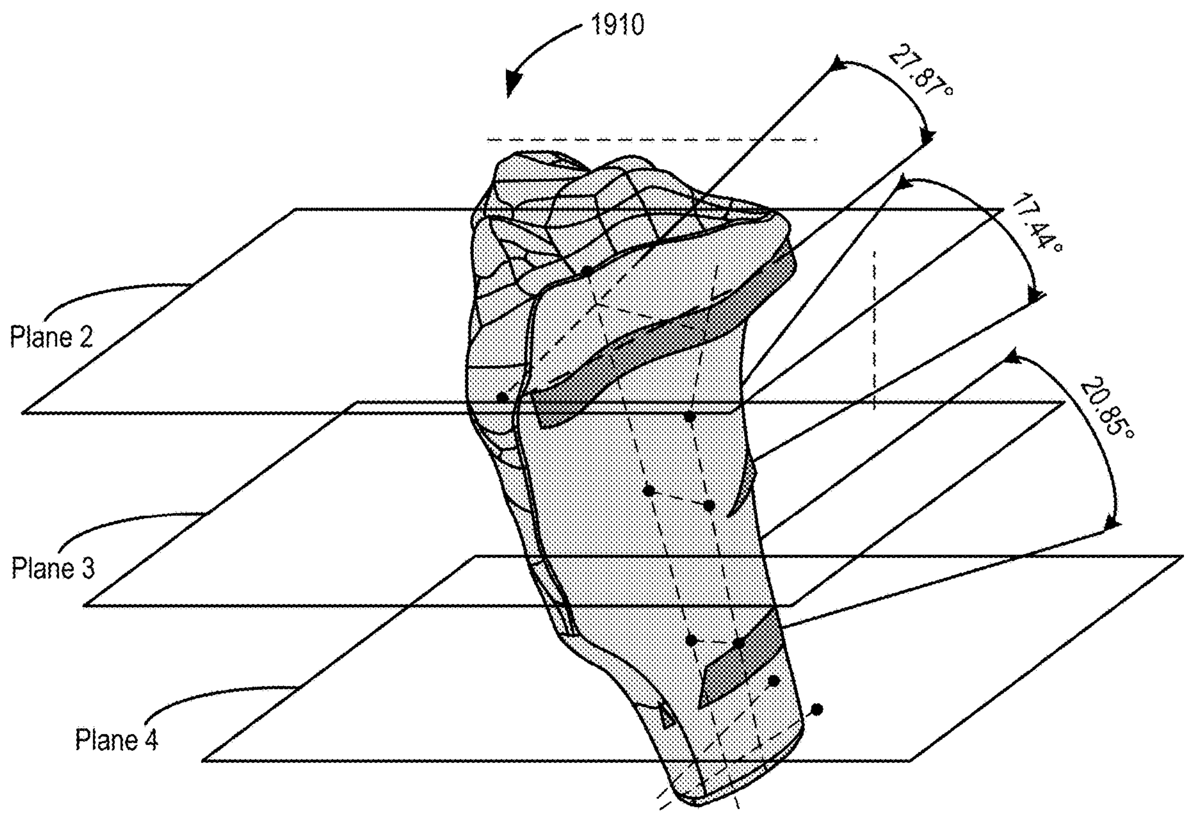
FIG.19

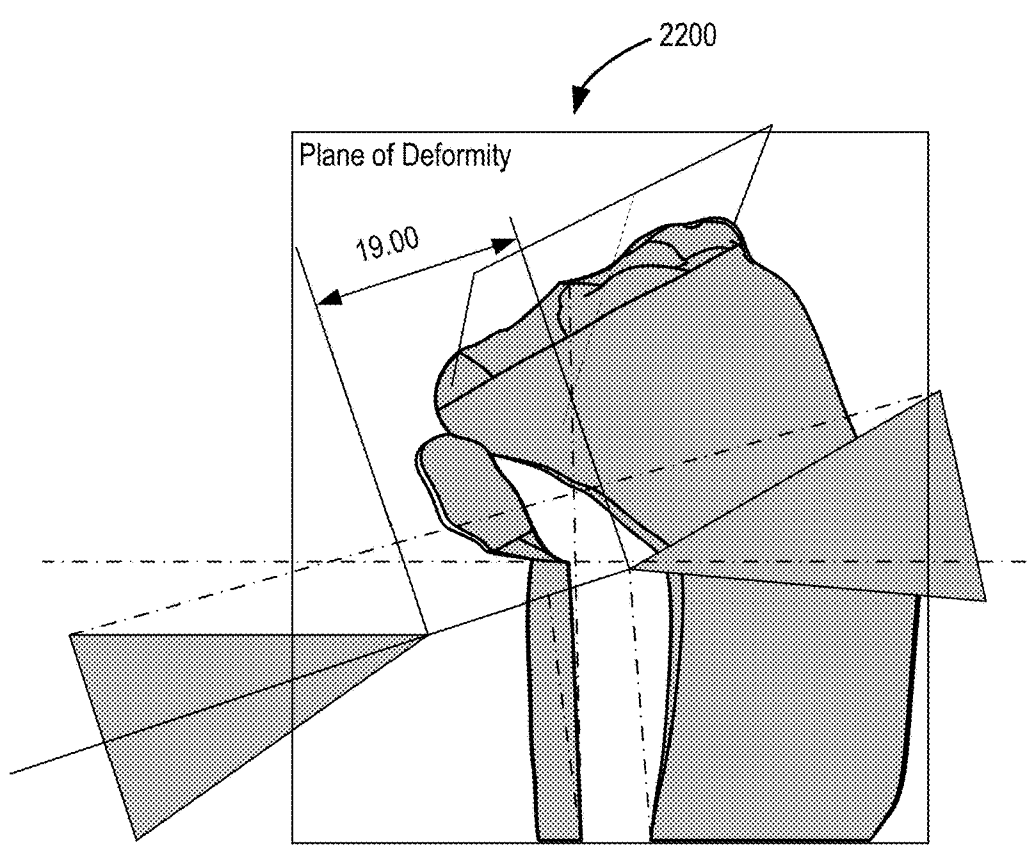
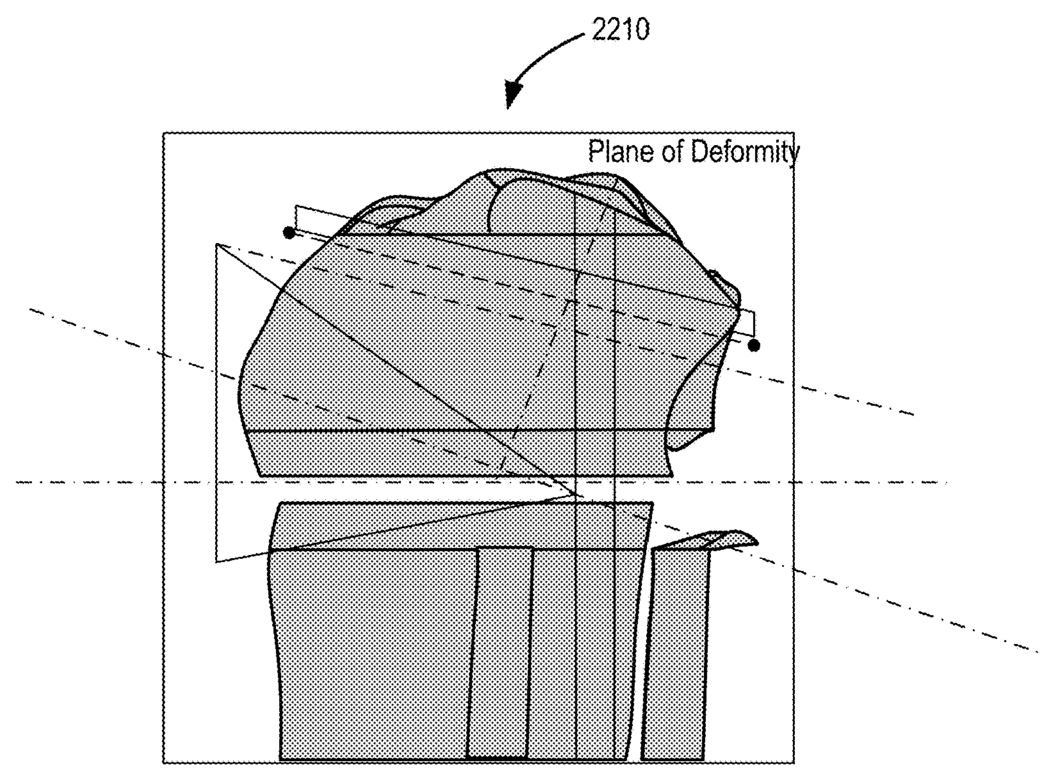
FIG. 22

CONFORMATION BASED BONE MODEL GENERATION AND ASSOCIATED SURGICAL TECHNIQUES

CROSS REFERENCE TO RELATED APPLICATIONS

This application claims the benefit of U.S. Provisional Patent Application No. 63/431,093, filed Dec. 8, 2022, which is incorporated by reference herein in its entirety for all purposes.

BACKGROUND

The application of computer modeling and three-dimensional printing in orthopedics continues to evolve. Traditional uses of such technologies include surgical education, preoperative planning, and procedure rehearsal. Furthermore, the efficacy of intraoperative patient-specific surgical equipment is being reported more commonly. For example, the use of three-dimensional printed anatomic guides, osteotomy guides, bone alignment guides, and drill guides, as well as other various custom implants, have been demonstrated in vivo. Advantages of these custom surgical instruments specific to a patient's anatomy include improved surgical precision, reduced intraoperative decision making and surgical duration, and avoidance of harmful intraoperative radiation.

Despite reports of success with patient-specific surgical equipment thus far, several key limitations exist. These limitations include inaccurate modeling of the anatomic features for which the patient-specific surgical equipment is being designed for. The accuracy of three-dimensional printed anatomic guides that are meant to interface with anatomic features depend on the resolution achieved in source images of those anatomic features. Generally, the source data used for three-dimensional modeling and printing of patient-specific surgical equipment are derived from computed tomography (CT) images. However, the minimum voxel size of conventional CT is orders of magnitude larger than the finely detailed images that modeling and printing software are capable of rendering. This lack of detail can lead to geometric inaccuracy when applied to the generation of patient-specific surgical equipment. CTs are generated using slices of an imaged object where the slice thickness is normally in the range of sub-millimeter to 5-millimeter thick. While attempts to smooth pixelated images in modeling software can help to partially alleviate issues with image slices having larger dimensions, they also have a tendency to further disrupt the geometric accuracy of anatomic landmarks.

The drawbacks associated with inaccurate imaging discussed in the prior paragraph are suffered in addition to the time, radiation exposure, and cost barriers already associated with obtaining CT imaging in the first place. As such, technologies and techniques that minimize, or eliminate, the need for advanced multi-planar imaging in the development of patient-specific surgical equipment are important as they can help to increase the accessibility of patient-specific surgical equipment and associated treatments.

SUMMARY

Methods and systems related to bone model generation and associated surgical techniques are discussed herein. In specific embodiments of the invention, the bone model generation is conducted using a conforming bone template model and a measured nonconformity of the patient bone. In specific embodiments of the invention, the measured nonconformity of the patient bone is measured by a surgeon or other healthcare professional and is entered into a bone model generation system. The bone model generation system can be part of a design environment. As used herein, an operator of such a system is referred to as an operator. The bone model generation systems disclosed herein can produce accurate models of a patient's bone by essentially modifying the conforming bone template model with the measured nonconformity. Once generated, the bone models can be used for, among other applications, preoperative planning and the potential generation of patient-specific surgical implements such as implants, customized jigs, and surgical guides.

In specific embodiments of the invention, advanced multi-planar imaging is not required to generate a bone model of a patient's bone. In specific embodiments of the invention, a model of a patient's bone as created by the bone model generation systems disclosed herein is more accurate and useful than a model that would otherwise have been created through complex imaging and passing the imaging data through an image processing pipeline. Patient bones generally conform to a large degree to a template bone except for the existence of a given nonconformity of interest. This fact is leveraged by specific embodiments of the invention that avoid the need to capture and process superfluous data such as a precise description of the anatomic landmarks of a patient's bone, and instead move directly from a description of the nonconformity to an actionable model of the patient's bone. In specific embodiments, the nonconformity is measured by an operator using x-ray imaging or some other imaging system that does not have the same limitations as CT imaging in terms of time, radiation exposure, and/or cost barriers. In specific embodiments, the nonconformity is measured by an operator using well established procedures for characterizing given nonconformities from standard planar images of a patient's bone such as standard orthogonal radiographs. As such, these embodiments leverage well established and agreed upon procedures that operators are used to dealing with in traditional medical practice in order to generate high fidelity actionable bone models for cutting edge preoperative planning techniques. In specific embodiments, the nonconformity is measured by an operator using a three-dimensional scan of the patient's limb. As such, these embodiments offer the benefit of zero radiation exposure and the cost barriers associated with radiographs while at the same time the approaches disclosed herein allow a nonconformity to be elucidated sufficiently with the obtained information.

In specific embodiments of the invention, a design environment is provided that allows for the intuitive generation of a patient-specific nonconformal bone model by an operator that is not accustomed to dealing with complex three-dimensional modeling flows. The design environment can include basic user interface elements such as selection boxes and text entry fields for making selections regarding the desired nonconformal bone model and for entering or selecting values for constraints on the model that can define a nonconformity. Additionally, the design environment can render the nonconformal bone model in real time so that an operator can iteratively specify the bone model and see the impact of their specifications on the bone model as they are entered. The feedback provided by such a system can increase the usability and user experience of the design environment particularly for those that are not accustomed to working with three-dimensional modeling tools.

In specific embodiments of the invention, the systems and methods disclosed herein which generate bone models can also be configured to quickly generate certain patient-specific surgical equipment (e.g., osteotomy guides). This functionality is possible because the nonconformity which will be addressed by that patient-specific surgical equipment has already been precisely defined within the model as a separate actionable entity. For example, as the angle of a bone deformity is already known and represented in an actionable model, the solution to that specific bone deformity, for that specific patient, can be solved for directly using that same actionable model.

In specific embodiments of the invention, a method for generating a bone model for a patient bone, in which each step is computer-implemented, is provided. The method comprises storing a conforming bone template model, accepting a measured nonconformity of the patient bone, and generating a nonconforming bone model using the measured nonconformity and the bone template model. The measured nonconformity is used to set a constraint of the conforming bone template model to a value and the nonconforming bone model has the value for the constraint.

Accordingly, in specific applications, a conforming bone template model is preconfigured to allow operators to define nonconformities succinctly and efficiently by setting one or more values of a conforming bone model to obtain a customized patient-specific bone model that can then be used for preoperative planning. In specific applications, the systems and methods disclosed herein further allow operators to conduct that preoperative planning using a similar paradigm of simply setting one or more values in a design environment that displays images of aspects of the operation being planned. In specific applications, both the generation of the nonconforming bone model and the preoperative planning can be conducted in an iterative manner where values are entered in the design environment and images of the bone model or aspects of the operation are displayed to the operator as values are received.

BRIEF DESCRIPTION OF THE DRAWINGS

The accompanying drawings illustrate various embodiments of systems, methods, and embodiments of various other aspects of the disclosure. A person with ordinary skills in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 3 illustrates a design environment for generating a nonconforming bone model in accordance with specific embodiments of the inventions disclosed herein.

FIG. 11 illustrates a user interface for observing the true plane and magnitude of a deformity with orthogonal nonconformities specified in accordance with specific embodiments of the inventions disclosed herein.

FIG. 15 illustrates a user interface for accepting a segmented bone segment scaling factor in accordance with specific embodiments of the inventions disclosed herein.

FIG. 17 illustrates the lofting of two segmented bone segments into a nonconforming bone model in accordance with specific embodiments of the inventions disclosed herein.

FIG. 18 illustrates various planes and parameters associated with the generation of a nonconforming bone model with a nonconforming medial tibial cortex in accordance with specific embodiments of the inventions disclosed herein.

FIG. 19 illustrates an approach for calculating the offsets required to generate a nonconforming bone model with a nonconforming medial tibial cortex in accordance with specific embodiments of the inventions disclosed herein.

FIG. 22 illustrates a post-operative bone model generated using the model of the cut guide generated in the flow chart of FIG. 21 in accordance with specific embodiments of the inventions disclosed herein.

DETAILED DESCRIPTION

Figure 1:
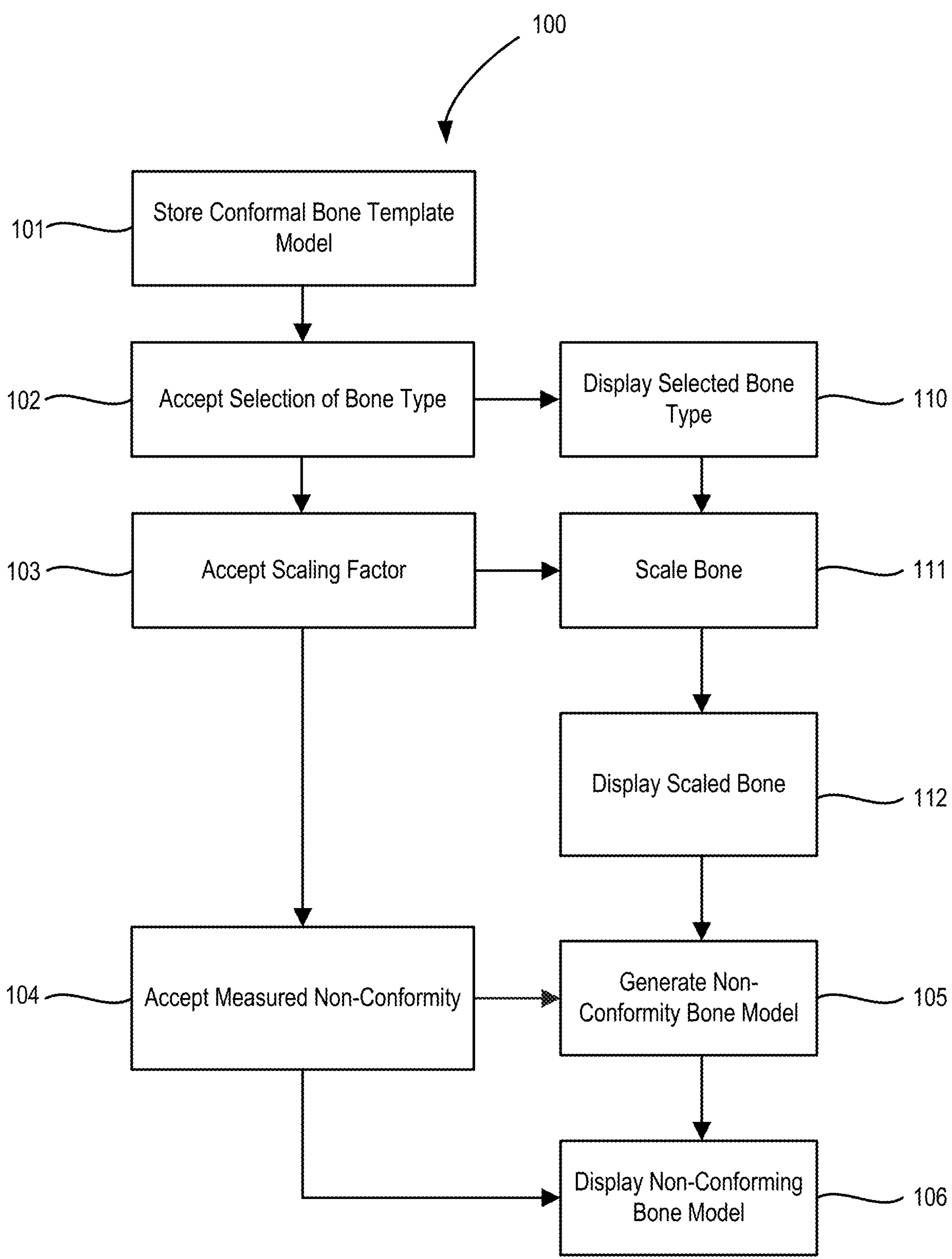
FIG. 1 illustrates a flow chart for a set of methods for generating a nonconforming bone model in accordance with specific embodiments of the inventions disclosed herein.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Methods and systems which involve bone models and bone model generators are disclosed in detail herein. The methods and systems disclosed in this section are nonlimiting embodiments of the invention, are provided for explanatory purposes only, and should not be used to constrict the full scope of the invention. It is to be understood that the disclosed embodiments may or may not overlap with each other. Thus, part of one embodiment, or specific embodiments thereof, may or may not fall within the ambit of another, or specific embodiments thereof, and vice versa. Different embodiments from different aspects may be combined or practiced separately. Many different combinations and sub-combinations of the representative embodiments shown within the broad framework of this invention, that may be apparent to those skilled in the art but not explicitly shown or described, should not be construed as precluded.

Specific embodiments of the invention disclosed herein are described with respect to the generation of bone models for purposes of correcting angular limb deformities using patient-specific surgical equipment. Furthermore, specific embodiments of the invention disclosed herein are described with respect to the generation of bone models for the purpose of planning a tibial plateau leveling osteotomy (TPLO). However, the approaches disclosed herein are more broadly applicable to bones having any form of nonconformity and various surgical and medical procedures as well as for medical professional training, product development, and other applications where the availability of nonconforming bone models are helpful.

Many orthopedic procedures, particularly with reference to limb conformation, involve a series of objective measurements and mathematic/trigonometric functions that define a patient's spatial conformation. There is a correct way to achieve conformation and a proper execution of the procedure involves achieving that objectively correct approach while minimizing error. However, in current limb deformity correction procedures using patient-specific surgical equipment, there are several key areas where human error may be introduced. The process involves defining and measuring the deformity in the patient, converting the patient's imaging to three-dimensional data, defining the deformity in the three-dimensional data, and can also include manipulating the three-dimensional data further through a processing pipeline until it is an actionable model for purposes of designing the patient-specific surgical equipment. Errors can be introduced at any of these stages using the current approach.

Measuring a deformity and defining it in three-dimensional data using current approaches is an error prone process. The process involves the derivation of complementary, objective, measurements from orthogonal radiographs and CT multi-planar reconstruction (MPR) images. It is a well-established process to describe a patient's osseous conformation and elucidate the true plane/magnitude of their deformity, if present, using the current literature and images of the deformity in standard orthogonal radiographs. However, a surgeon or other medical professional does not have the benefit of a well-established body of literature when it comes to documenting and describing a patient's osseous conformation using CT MPR images. Also, the measurements can vary significantly between adjacent CT MPR images which create a degree of uncertainty for the surgeon. This can cause the surgeon to default to the orthogonal radiographs and work to make the CT MPR frames selected "fit" that which was obtained on the orthogonal radiographic measurements. This same uncertainty and error exist, with even greater magnitude, as the surgeon tries to replicate the orthogonal spatial planes and objective measurements of the deformity in the patient's three-dimensional mesh rendering. Additionally, error can exist as the surgeon, or other medical professional, attempts to elucidate the true plane/magnitude of the deformity and generate a surgical guide within the mesh file.

Specific embodiments of the invention disclosed herein solve the problems described in the prior paragraph by avoiding the need to create a model from complex imaging of a patient's bone. Instead, a description of a deformity, which can be obtained from standard orthogonal radiographs, is used with a mathematically constrained generic bone template, to generate a three-dimensional rendering in the form of an actionable computer aided design (CAD) file, based on the patient's objective measurements that define their osseous conformation. The system can also be used to automatically produce patient-specific surgical equipment such as a patient-specific surgical guide. This can be done without the need to create a mesh file of the patient's bone as derived through laborious and generally unguided research conducted on complex image files of the patient's bone.

In specific embodiments of the invention, the techniques described are specific to the deformity the surgeon is presented with, not the surface topography of the patient affected by the deformity. As a result, complex imaging that is used to define patient-specific surgical equipment that is conformal to a bone surface is not required. As such, traditional orthogonal radiographs provide sufficient information for generating the required patient-specific surgical equipment.

Specific embodiments disclosed herein included automated systems that will mathematically derive a three-dimensional rendering of a patient's bone from the objective parameters that describe the bone's nonconformity, as well as generate a CAD model of patient-specific surgical equipment that can be used to correct the nonconformity. Specific embodiments of the invention therefore demonstrate that a fully defined/constrained three-dimensional rendering of a long bone may be produced without the need for CT imaging and have the capability to reduce the potential error associated with the human operator handling/transferring data. Additionally, specific embodiments obviate the barrier of the operator of the design environment needing to know how to generate mesh models or CAD models, as the process skips directly from a definition of a nonconformity using traditional measurement techniques to an actionable CAD model of the bone, and, in some embodiments, the patient-specific surgical equipment is also automatically generated.

FIG. 1 illustrates a flow chart 100 for a set of methods for generating a bone model for a patient bone, in which each step is computer-implemented. The steps can be conducted by one or more processors executing a set of executable instructions stored on a non-transitory computer readable medium. The one or more processors and the set of executable instructions can be used to instantiate a design environment with a user interface for entering specifications for a desired bone model. The steps of flow chart 100 involve accepting inputs from an operator and modifying a stored bone model based on those inputs to generate a revised bone model. As such, the steps can further be executed in combination with a data store which stored the unmodified bone model and which can store the generated bone model, and a bone model generator engine which can modify the bone model and generate the updated model for rendering.

The user interface of the design environment can include various user interface elements for accepting inputs from a user such as text input fields, selection buttons, drop down menus, or more complex user interface elements such as those used in three-dimensional modeling software to select, manipulate, and add or subtract from three-dimensional models. However, in specific embodiments of the invention, the user interface elements are limited to a simple set that can be utilized by an operator that does not have knowledge of standard three-dimensional modeling tools. For example, the user interface elements could be limited to a wizard or pull-down menu for selecting a bone model and a set of text inputs or value selectors for accepting standard values for defining a nonconformity of a bone that can be obtained from standard radiographs. In specific embodiments of the invention, the design environment can include a spreadsheet with cells that are labeled for the input of specific values used to define the bone model being worked on. For example, the design environment can include Microsoft Excel spreadsheets, with certain fields locked from usage by an operator, along with associated software such as Microsoft Virtual Basic scripts for interfacing the spreadsheet and user interface elements with a bone model generator engine and other elements of the design environment.

The design environment can also include an image rendering area for rendering an image of a bone model as it is being specified by a user. The image rendering area can allow an operator to review the impact of their inputs on the model in real time to further assist operators that have little experience with three-dimensional modeling software. In specific embodiments of the invention, the image rendering area can accept inputs that select and manipulate the bone model to allow the operator to inspect the model from certain angles or levels of zoom. In specific embodiments, the image rendering area can accept inputs that further specify the model or manipulate the model for viewing. In these embodiments, the inputs on the image rendering area can be mirrored by changes in the user interface elements that accept specifications of the bone model such that any displayed values in those user interface elements remain synchronized with the status of the bone model. In specific embodiments in which the design environment is also used to produce patient-specific surgical elements or to model specific states of a bone during preoperative surgical planning, the image rendering area can also render images of that patient-specific surgical equipment and bone model states.

In specific embodiments, the design environment can include a bone model generation and manipulation engine. The bone model generation and manipulation engine can take in the inputs provided by the operator and stored models of the bones that are available to the manipulation engine in a data store and generate modified versions of the stored models based on those inputs. The bone model generation and manipulation engine can operate in real time to continue to render an updated version of the bone model in the image rendering area. In specific embodiments of the invention, the bone model generation and manipulation engine can be implemented using scripts written for SolidWorks and an API for accepting inputs from the user interface and outputting the current bone model based on those received inputs.

Flow chart 100 includes step 101 of storing a conforming bone template model. The conforming bone template model can be part of a library of bones that are stored in a data store that is accessible to the design environment. The conforming bone template models can be representative of canonical bones of specific types that can serve as the basis for generating patient-specific bones using the design environment. The term conforming is used for these bone template models because they conform to standard anatomical expectations regarding a given bone. In specific embodiments, the conforming bone templates in the library can be associated with different species (e.g., human or canine). In specific embodiments, the conforming bone template models in the library can be associated with different genders, ages, and other demographic categories. However, much of the variation attributable to demographic categories can instead be provided to operators in the form of scaling factors that can be specified by the operators, in accordance with further steps of the flow chart described below, and the library of conforming bone template models can be kept to a reasonable size by allowing operators to utilize such scaling factors. The models can be constructed from a scan of one or more canonical examples of a bone having the desired characteristics of the model (e.g., bone type, species, etc.).

The conforming bone template models can be mathematically constrained conforming bone template models where the various surfaces of the bones are defined algorithmically based on specific parameters. For example, the model could define the surfaces using a scalable vector graphics format. The models can include a layer of parameters above those that define the surfaces of the model which are used to derive the lower layer of values. This higher layer of parameters could be based on standard measurements of the bone in question as used by the medical profession such as the length of the bone and the sagittal and frontal plane spans of the bones at specific slices along the transverse plane. This higher layer of parameters could be surfaced to the operator of the design environment for scaling as described below. The standard measurements could be measurements that are standard in the medical profession of describing the size of a bone given standard planar radiographs.

The conforming bone template models could include definitions for specific well-known features of a given bone. The definitions could include stored locations that are elements of the models. The stored locations could be anatomical features of the given bone that are used for preoperative and intraoperative measurements in surgical and anatomical literature. For example, the model could include a location for the intercondylar eminence of a tibia. The definitions could include vectors that are elements of the models. For example, the mechanical axis of a given bone could be defined using both a stored location and pose of the vector within the model relative to that stored location.

The conforming bone template models could be defined by a singular closed surface extending for as long as possible before the more complex features proximate to the joints of the bones are reached. The singular closed surface could provide a singular perimeter when bisected along the length of the conforming bone template model. In specific embodiments of the invention, this aspect of the conforming bone template models provides substantial benefits. The ability of the model to be bisected and provide singular perimeters at the end of each of the newly formed and bisected bone segments provide significant benefits in terms of facilitating the definition of a deformity or in terms of manipulating a model of a bone that is segmented via an osteotomy in accordance with the processes disclosed below.

Flow chart 100 continues with step 102 of accepting a selection of a bone type. The selection can be provided by a user in a design environment. The selection can be provided via a user interface element such as a drop-down menu listing a set of potential bones. The user interface can also include inputs for a species of the patient associated with the modeled bone or demographic information of the patient associated with the modeled bone. These inputs can then be used to select the appropriate conformal bone template model from memory. Methods in accordance with flow chart 100 can include a step of displaying 110, before step 103 of accepting a measured nonconformity and after step 102, the conforming bone template model of the selected bone type.

Figure 2:
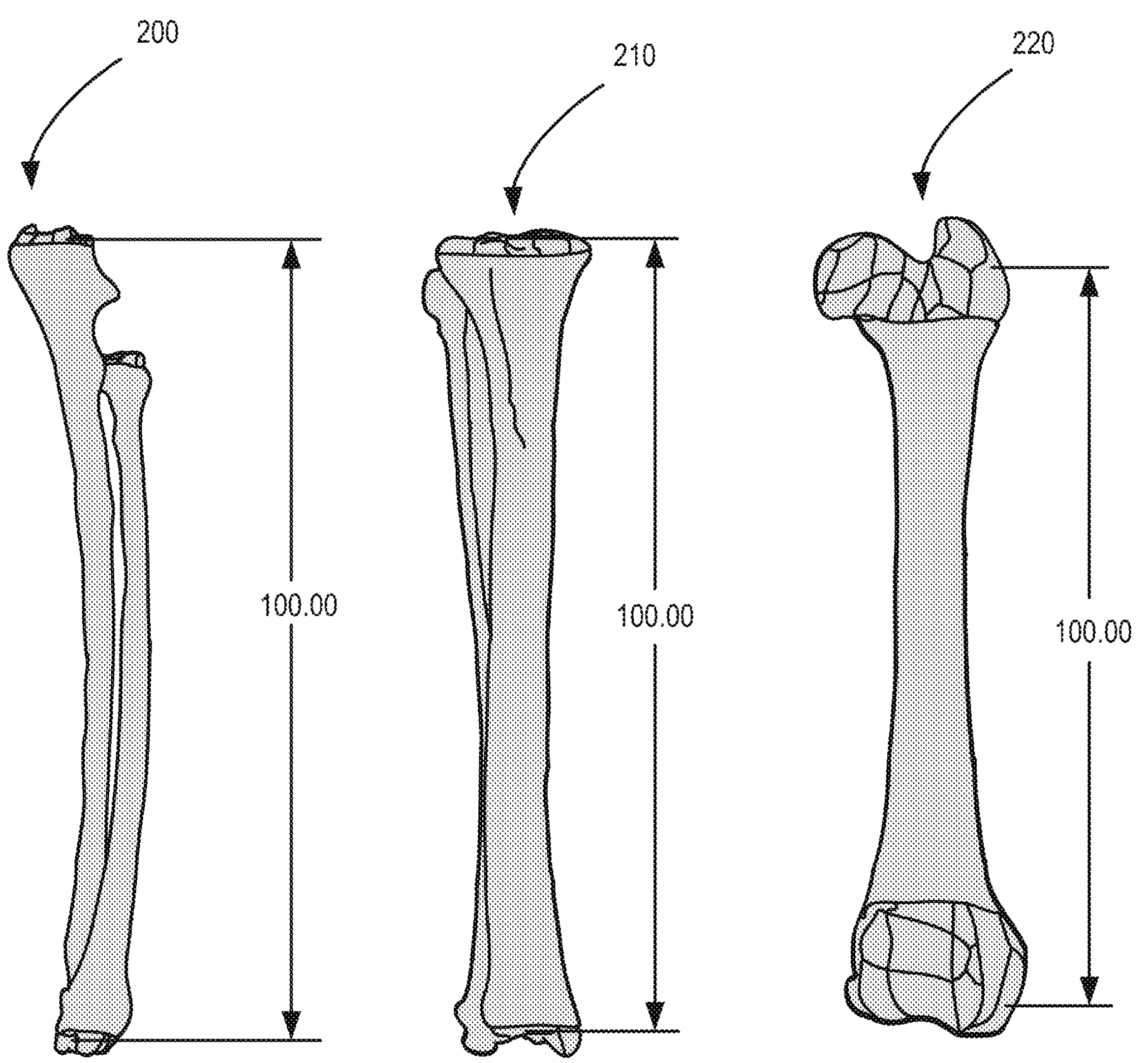
FIG. 2 illustrates a set of conforming bone model templates in accordance with specific embodiment of the inventions disclosed herein.

FIG. 2 illustrates three conforming bone template models that can be selected in a design environment by an operator. Model 200 is of a radius and ulna. Model 210 is of a tibia and fibula. Model 220 is of a femur. The models can be presented for selection by the user as they appear in FIG. 2 or in a list format with the name of the bones as selectable items in the list. The illustrated models include a collection of surfaces that are connected and mathematically constrained. The surfaces are illustrated by black lines on the illustrated models. As seen, each model conforms with the requirements mentioned above regarding how the central part of the bone can advantageously be one singular closed surface that can provide a singular perimeter—defined by a cross section of the closed surface at any point along the surface. Accordingly, bisections along this surface of the model can be used with the approaches disclosed below in which deformities are defined on bisected bones or surgeries including bisected bones are planned. As labeled, each model includes a default length of 100 mm. This default template length can be changed to any other value, as long as the formulas for the scalar calculations are updated to reflect that value. Applying the scalar to the template results in a bone model reflecting the length input by the user. FIG. 3 illustrates a design environment 300 with a user interface for specifying specific characteristics of a bone 301 along with a rendering area 302 which includes a rendering of a conforming bone template model. The design environment screen in FIG. 3 can be presented as soon as a user selects a bone template model.

FIG. 1 continues with step 103 of selecting a scaling factor. The scaling factor can take on various forms. The scaling factor can be as simple as a desired length of the patient bone. As such, the scaling factor can be a single scalar number that is entered by the operator. However, the scaling factor can also be multidimensional and include a scalar for scaling the overall size of the bone and additional scalars for scaling the frontal plane extent of the bone at one or more points and/or scaling the sagittal plane extent of the bone at one or more points. In embodiments in which the scaling factor is the length, or some other dimension of the bone, the scaling factor can be precisely defined with respect to standard anatomical measurement techniques in the industry. For example, if the scaling factor were a length of a tibia, the length could be defined in the conforming bone template model as the distance between the intercondylar eminence and the distal intermediate ridge, at the proximal and distal limits respectively, of the tibia as shown in model 210. In specific embodiments, the scaling factor can include more parameters which can be specified to create canonical bones having dimensions that match those of a patient bone. The conformal bone template models can include these adjustable parameters with respect to each bone in the library. The scaling factor could include at least one of a frontal scaling factor defining a scaling factor for the extent of the bone in the frontal plane and a sagittal scaling factor defining a scaling factor for the extent of the bone in the sagittal plane. The scaling factor scalars for the frontal and sagittal plane could apply to scaling the bone only at specific points such as proximate the joints. The scaling factor scalars could include frontal and sagittal scaling factors for multiple points along the extent of the bone.

Figure 4:
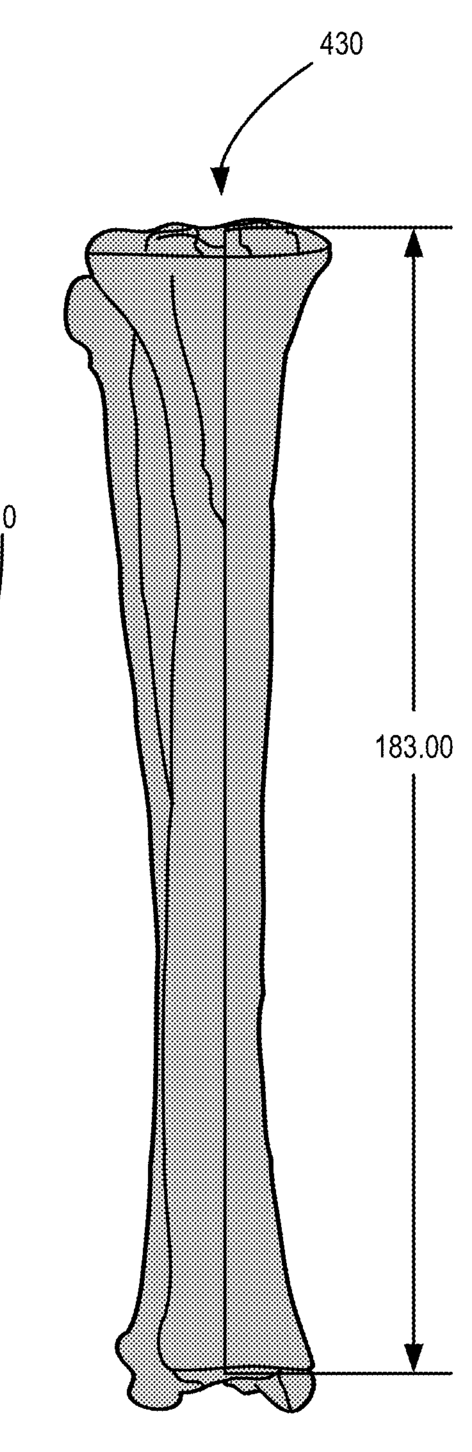
FIG. 4 illustrates a scaled conforming bone model and a user interface for specifying a scaling factor in accordance with specific embodiments of the inventions disclosed herein.

Step 103 can be followed by step 111 of scaling the conforming bone template model by the scaling factor to produce a scaled conforming bone template model. The conforming bone template model can include mathematical definitions for how the various dimensions and surfaces of the conforming bone template model should scale with the scaling factor. Each model can be scaled and oriented to a predetermined reference scale and planar orientation so that it can easily be scaled to a new size by scaling the reference model by the ratio of the desired size to the size of the reference model. FIG. 4 illustrates a user interface 410 for entering a scaling factor for a conforming bone template model. As seen in user interface element 420, the scaling factor includes a desired bone height, a frontal plane scale factor, and a sagittal plane scale factor.

Step 111 can be followed by step 112 of displaying, prior to accepting a measured nonconformity and after accepting the scaling factor, the scaled conforming bone template model. Referring to FIG. 4, the resulting scaled conforming bone template model is displayed in display area 430. As illustrated, the scaled conforming bone template model has a length of 183 mm. The scaled conforming bone template model is similar in all respects to the conforming bone template model with the exception that the default value for the length parameter has been changed. Except for that modification, the model can be similar in that it is rendered and scaled using the length 183 mm and a set of mathematical calculations that determine different proportions in the model as the scaled conforming bone template model is being rendered.

Flow chart 100 continues with step 104 of accepting a nonconformity of the patient bone. The nonconformity can be a measured nonconformity on an actual patient bone or a hypothetical nonconformity for which a bone model is being generated. The nonconformity can be a break, deformity, or other nonconformity. The nonconformity can be defined as an inappropriate positioning of bone segments containing one or more deformity apexes, or centers of rotation angulation (CORAs). The degree of torsion, varus or valgus, and procurvatum or recurvatum unique to a given deformity can be measured, allowing for objective characterization and functional recreation of long bone deformities. For example, in the case where the nonconformity is a deformity, an operator may be able to provide a measured magnitude of deformity obtained from each orthogonal plane in addition to the location of any CORAs, and the true plane of deformity and its magnitude could be automatically calculated based off those values and the conformal bone template model. The values that comprise a description of the measured nonconformity can include a distance from a joint at which the nonconformity occurs, a point at which the nonconformity occurs given in a frame of reference relative to the plane of the joint or other aspect of the bone, or any frame of reference in which the bone is being considered.

The measured nonconformity can be accepted in the form of a set of numbers that are entered via user interface elements of the design environment. For example, the user interface elements can be input fields into which the values are entered or selection interfaces on which the values are selected. The set of numbers can include a distance of a nonconformity from a joint of the patient bone or another landmark on the patient bone. The user interface elements can be labeled in the design environment to indicate which specific values are required for a given input and can include links to descriptions of how the value can be measured. The set of numbers can also include an angle in the sagittal plane and/or an angle in the frontal plane that define(s) the direction of the nonconformity. In specific embodiments, the nonconformity can be accepted in the form of a plane of the deformity and a magnitude of the deformity. The plane of the deformity can be provided in the form of two angles relative to a frontal and sagittal plane of the joint. As another example, the set of numbers can include a torsional deformity factor defining the rotation of the bone in the coronal plane relative to the conformal bone model. In specific embodiments, the user interface will solely accept a torsional deformity factor and a location at which the rotation begins and ends relative to the location of the nearest joint. While the example of numerical inputs provided to a set of fields were provided as an example of a user interface in this example, alternative approaches can use interfaces with different characteristics such as selection, rotation, select and drag to resize, and other interfaces used to manipulate three dimensional objects in a WSIWIG environment can be utilized in the alternative or in combination.

In specific embodiments, the set of values that define the deformity can set multiple constraints of the conformal bone model. For example, a first constraint of the conforming bone template model can be a distance from a joint to the plane of the deformity and the measured nonconformity can be used to set a second constraint of the conforming bone template model to a second value where the nonconforming bone model has the second value for the second constraint. The measured nonconformity can further be used to set a third constraint of the conforming bone template model to a third value and the nonconforming bone model can have the third value for the third constraint. The second constraint of the conforming bone template model can be a magnitude of the deformity expressed as an angle in the sagittal plane. The third constraint of the conforming bone template model can be a magnitude of the deformity expressed as an angle in the frontal plane. Multiple sets of such values can be constraints of the conforming bone template model as the model can be designed to accept multiple sets of values that each define a different deformity of a nonconforming bone.

Figure 5:
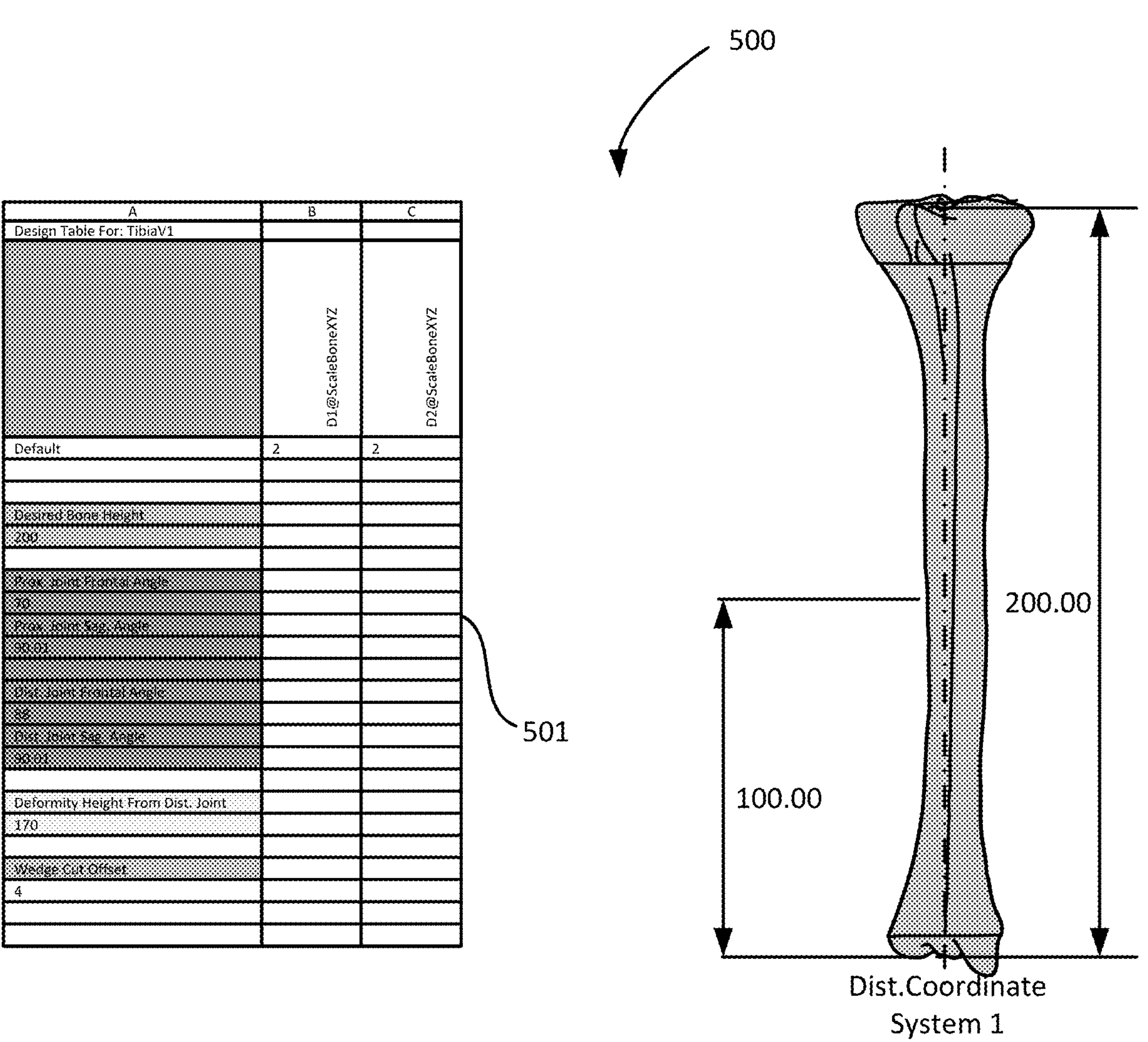
FIG. 5 illustrates a user interface for specifying a nonconformity in a frontal plane in accordance with specific embodiments of the inventions disclosed herein.
Figure 6:
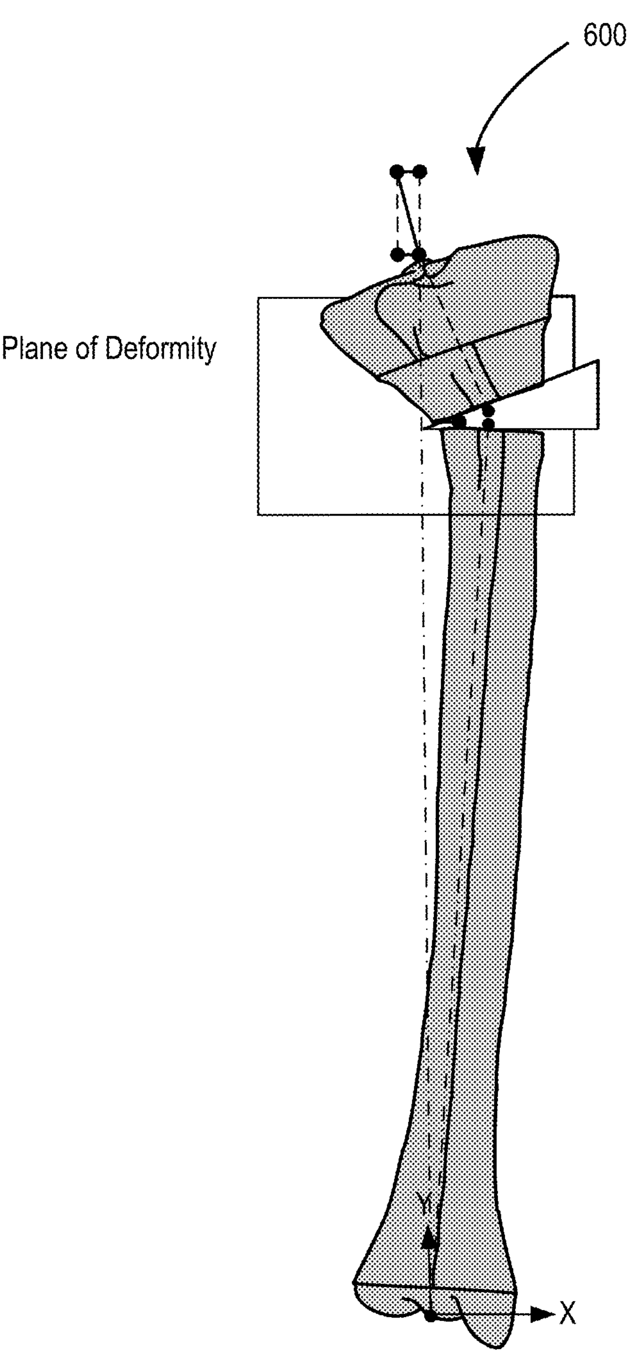
FIG. 6 illustrates a nonconforming bone model with a positive angle in the frontal plane in accordance with specific embodiments of the inventions disclosed herein.
Figure 7:
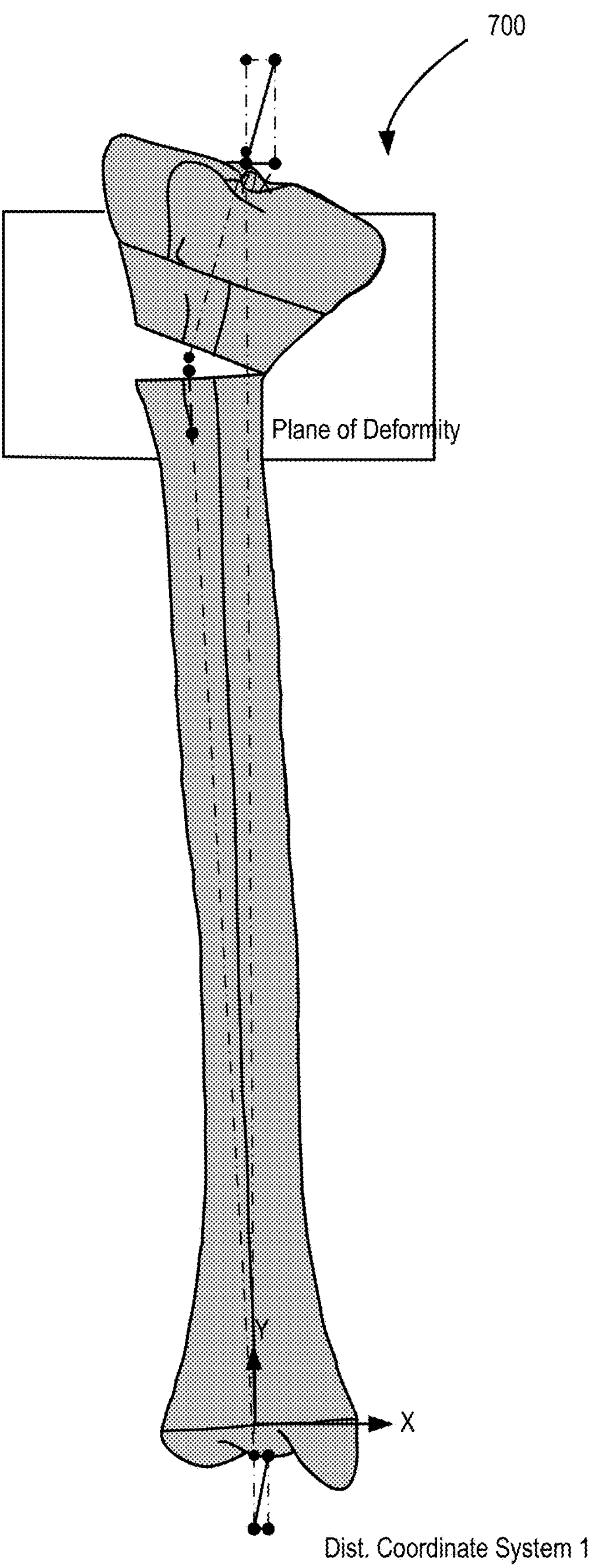
FIG. 7 illustrates a nonconforming bone model with a negative angle in the frontal plane in accordance with specific embodiments of the inventions disclosed herein.

In specific embodiments, the values that comprise a description of the nonconformity can be measured using traditional planar radiographs, a three-dimensional scan of the patient's limb coupled with a derived estimate of the deformity, or via CT imaging of a patient's bone. The bone template model library can be designed to include inputs to accept a definition of multiple different types of nonconformities using standard medical definitions for those deformities. For example, FIG. 5 illustrates a design environment 500 with a user interface 501 for accepting a deformity height from a distal joint, a proximal joint frontal angle, a proximal joint sagittal angle, a distal joint frontal angle, and a distal joint sagittal angle for a deformity. FIG. 5 also includes a frontal plane view of a conformal 200 mm tibia before the defined deformity has been applied. FIGS. 6 and 7 provide renderings of that bone model after it has subsequently had user inputs to create a 20-degree magnitude deformity in the positive direction 600, and negative direction 700 in the frontal plane. As illustrated, the deformity angles are defined by modifying the joint angle off 90 degrees with values that increase or decrease from that 90-degree value angling the bone segments in different directions relative to each other. As illustrated, in specific embodiments the angles can be specified with respect to either the proximal or distal joint with the sum of the difference from 90 degrees being equal to the total magnitude of the nonconformity.

Figure 8:
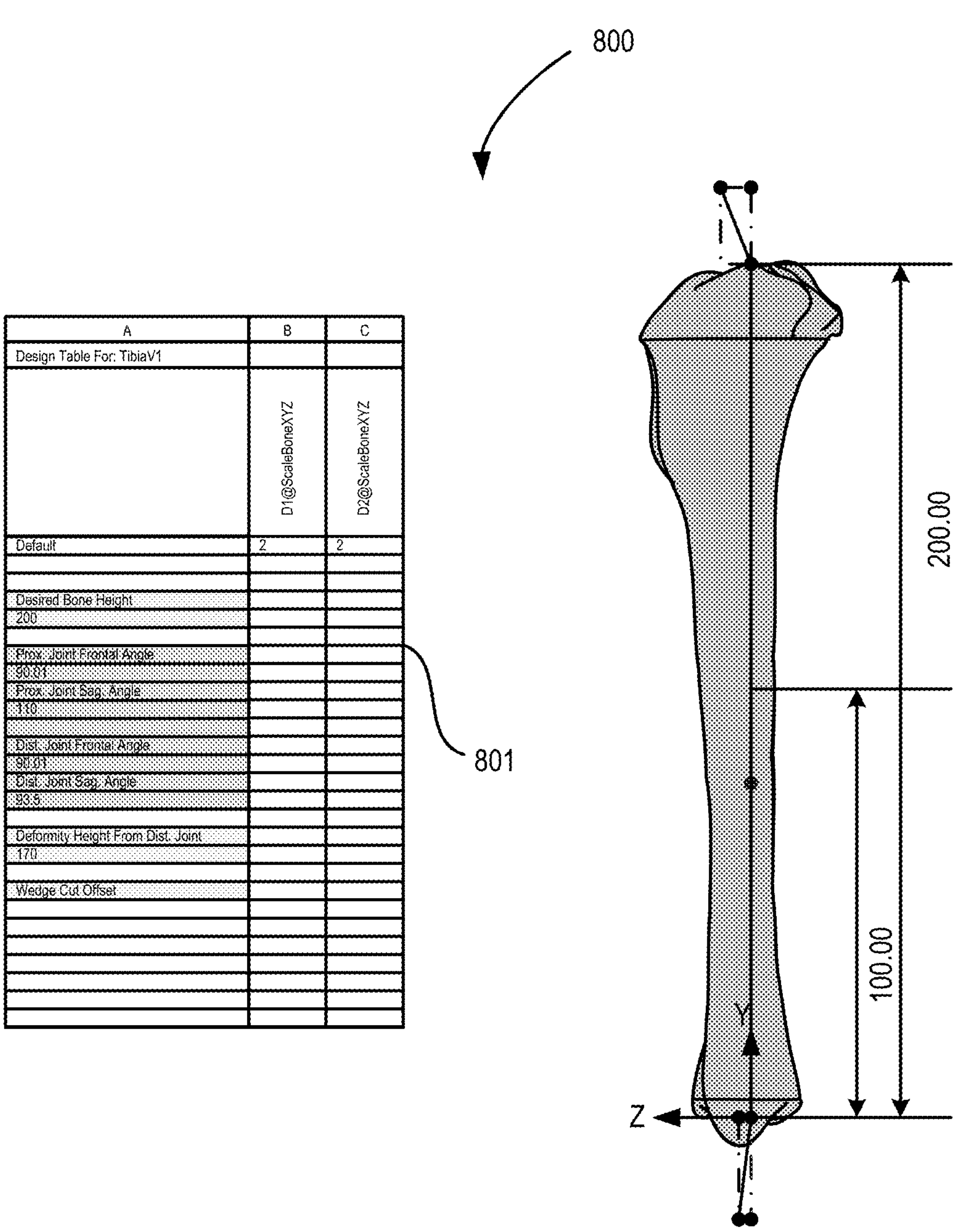
FIG. 8 illustrates a user interface for specifying a nonconformity in a sagittal plane in accordance with specific embodiments of the inventions disclosed herein.
Figure 9:
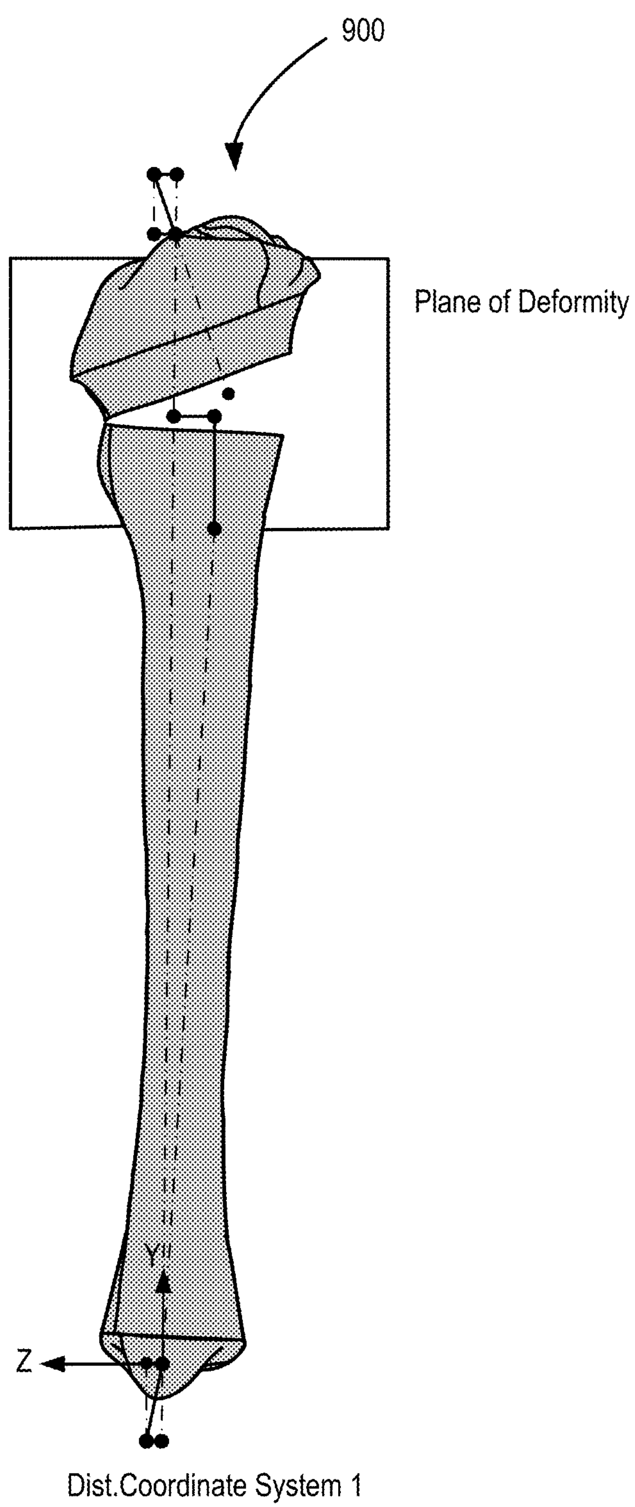
FIG. 9 illustrates a nonconforming bone model with a positive angle in the sagittal plane in accordance with specific embodiments of the inventions disclosed herein.
Figure 10:
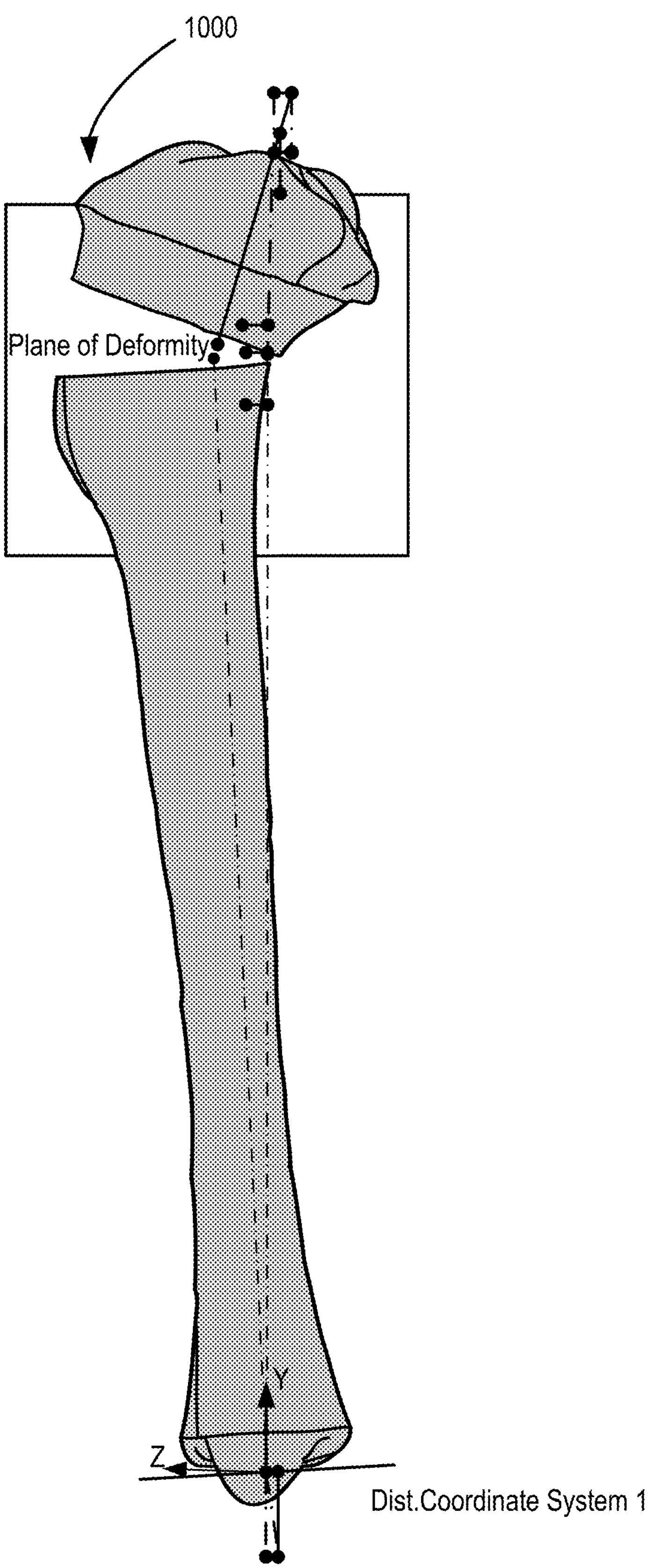
FIG. 10 illustrates a nonconforming bone model with a negative angle in the sagittal plane in accordance with specific embodiments of the inventions disclosed herein.
Figure 16:
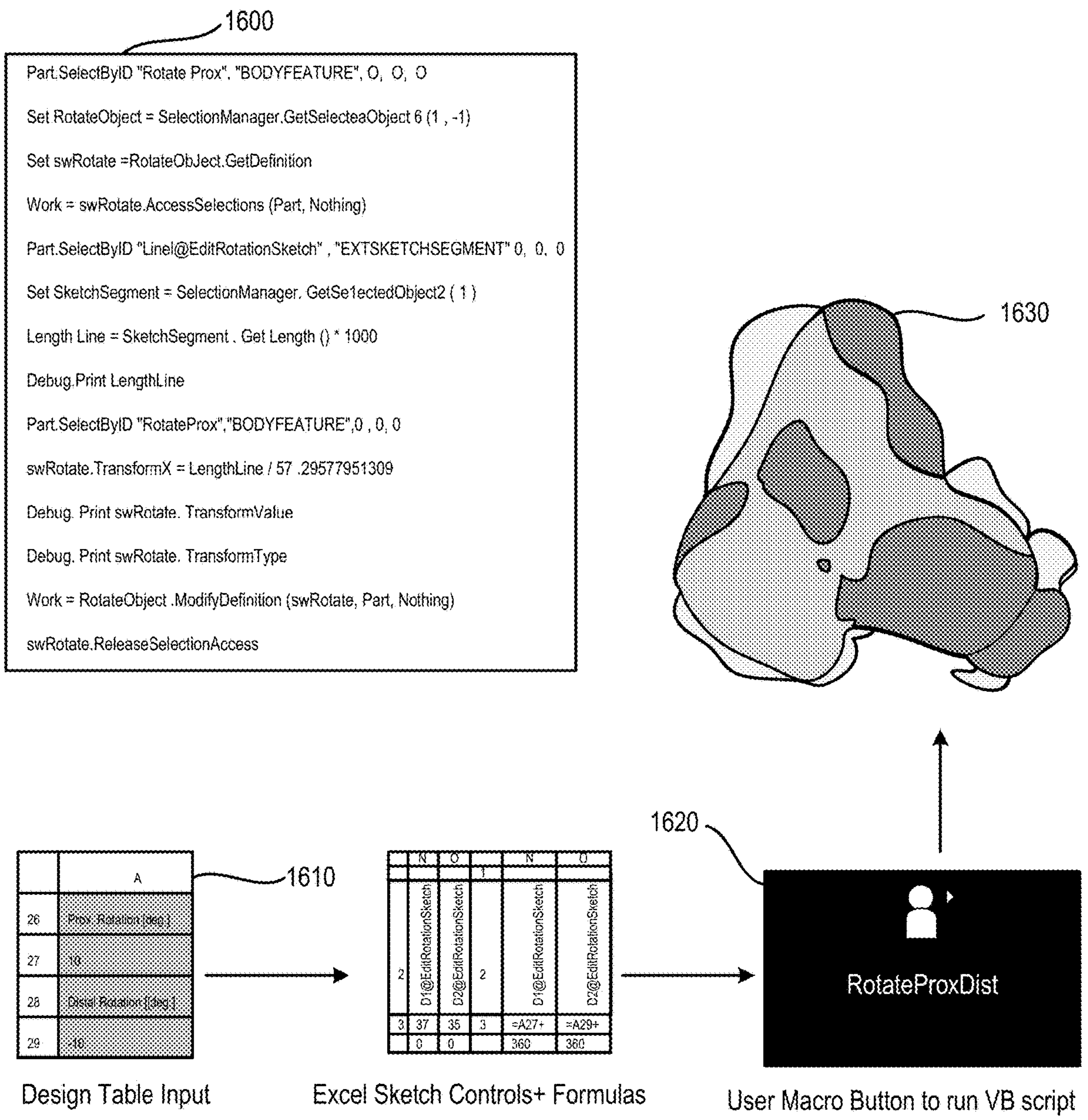
FIG. 16 illustrates an automated processing flow for generating a nonconforming bone model with a torsional nonconformity in accordance with specific embodiments of the inventions disclosed herein.

As another example, FIG. 8 illustrates a design environment 800 with a user interface 801 for accepting a deformity height from a distal joint, a proximal joint frontal angle, a proximal joint sagittal angle, a distal joint frontal angle, and a distal joint sagittal angle for a deformity. FIG. 8 also includes a sagittal plane view of a conformal 200 mm tibia before the defined deformity has been applied. FIG. 8 also shows how an original 100 mm tibia bone model template can be scaled to a 200 mm tibia bone model. FIGS. 9 and 10 provide renderings of that bone after it has subsequently received user inputs to create a 20-degree magnitude deformity in the positive direction 900 and negative direction 1000 in the sagittal plane. FIG. 16 shows torsion in the coronal plane (view 1630), wherein the unshaded proximal tibia has been rotates 10-degrees from its shaded original position, as directed by the operator in the design table input 1610 for the "Prox. Rotation (deg)." While each of these examples includes a single nonconformity, in specific embodiments, multiple nonconformities can be defined for a single patient. FIG. 11 shows a coronal plane view 1100 of a normal 200 mm tibia that has frontal and sagittal plane deformation magnitudes input by the operator as 23.5 degrees and 20 degrees respectively. As a direct output, the true plane, 25 degrees, and magnitude of deformity, 39.93 degrees of the frontal plane, are displayed as the singular resolution possible based upon the orthogonal biplanar deformity input by the operator.

Flow chart 100 continues with step 105 of generating a nonconforming bone model using the nonconformity of the patient bone and the bone template model. This step can be conducted by a bone model generation engine such as a three-dimensional modeling software such as SolidWorks with an API for accepting the inputs to the conforming bone model and applying the accepted nonconformity definition to the bone model. The accepted nonconformity can be used to set a constraint of the conforming bone template model to a value. For example, the conforming bone template model can include constraints which can be used to define the location, pose, and rotation of specific deformities in the bone which can be used to generate a nonconforming bone model as a modified version of the conforming bone template model. The nonconforming bone model can be similar to the conforming bone model with the exception that the nonconforming bone model has the value for the constraint.

Flow chart 100 continues with step 106 of displaying the nonconforming bone model. The step can be conducted iteratively while accepting a measured nonconformity in step 104 so that an operator can evaluate the impact of the definition for the nonconformity they have provided on a model of the bone. A second iteration of step 104 can thereby include accepting a revised measured nonconformity of the patient bone. A second iteration of step 105 can include generating a revised nonconforming bone model using the revised measured nonconformity. A second iteration of step 106 can include displaying the revised nonconforming bone model.

In specific embodiments of the invention, the bone template model and the nonconforming model are in a CAD file format. This file can have sketches that are based upon mathematical mapping of the bone which presents a joint surface (e.g., similar to how a topographic map can show you the geography) and sequential sketches along the length of the bone template model bone ending at the opposite joint surface. The CAD model can be modified by deleting or modifying a constraint of the model. The constraint can be surfaced to an operator of the system in order to allow them to define the constraint. Each time a constraint is operated, the sketch of the model may be updated to reflect the change. The operator can simply insert the parameter(s) that they are interested in rendering, and the resulting nonconforming bone model can be automatically rendered.

In specific embodiments of the invention disclosed herein a nonconforming bone model can be generated using a measured nonconformity and a bone template model. In specific embodiments of the invention, the bone template model or CAD template for a canonical bone can be used to make a model of a patient's bone using constraints that are added to a user interface such as the data sheet shown in FIG. 5. The CAD template can have an associated data sheet where such constraints (e.g., defined conformational parameters) may be replaced, based on what the operator has measured for their patient. This then automatically renders a new three-dimensional CAD bone, which is spatially/conformationally precise based upon those conformational parameters it has been provided with or already defined. The resulting process does not rely on "shape matching", "tracing", "converting", or "point cloud mapping" data for an existing bone's imaging data. Instead, the process produces a predictive three-dimensional CAD file of a bone's conformation that has its spatial parameters related to said conformation through mathematically defined parameters. The parameters then constrain the model and are alterable and are precisely defined in the model to support further operations such as the modeling of patient-specific surgical equipment.

Specific embodiments disclosed herein rely on spatially defining an affected bone and elucidating a nonconformity of the affected bone through previously established mathematical methods. These approaches are versatile and lend themselves to patients with preoperative imaging that permits the operator to objectively specify the associated parameters. Again, while the imaging used to obtain the associated parameters does not need to be CT imaging, the imaging data can be CT imaging or orthogonal radiographs, or any other software that allows the operator to define a nonconformity and provide it to the system. Specific embodiments carry the capacity to not only generate a three-dimensional rendering with numerical measurements being the only input but may also minimize error risk associated with a human operator and enable a wider array of people to serve as operators of the system by obviating the requirement for skills in computer modeling.

In specific embodiments of the invention, the measuring of the nonconformity by the operator and the accepting of the measured nonconformity of the patient's bone by the system can be conducted in various ways. In specific embodiments of the invention, the measuring is automated and is conducted based off image data. In alternative embodiments of the invention, the measuring is conducted by an operator conducting an evaluation of the patient. Preoperative diagnostic images can be utilized to characterize each nonconformity in terms of joint orientation angles, bone length, bone width at various locations and CORA. Torsion and joint rotation can be assessed using established techniques with CT images, if available, or via goniometry if radiographs were utilized alone.

Figure 12:
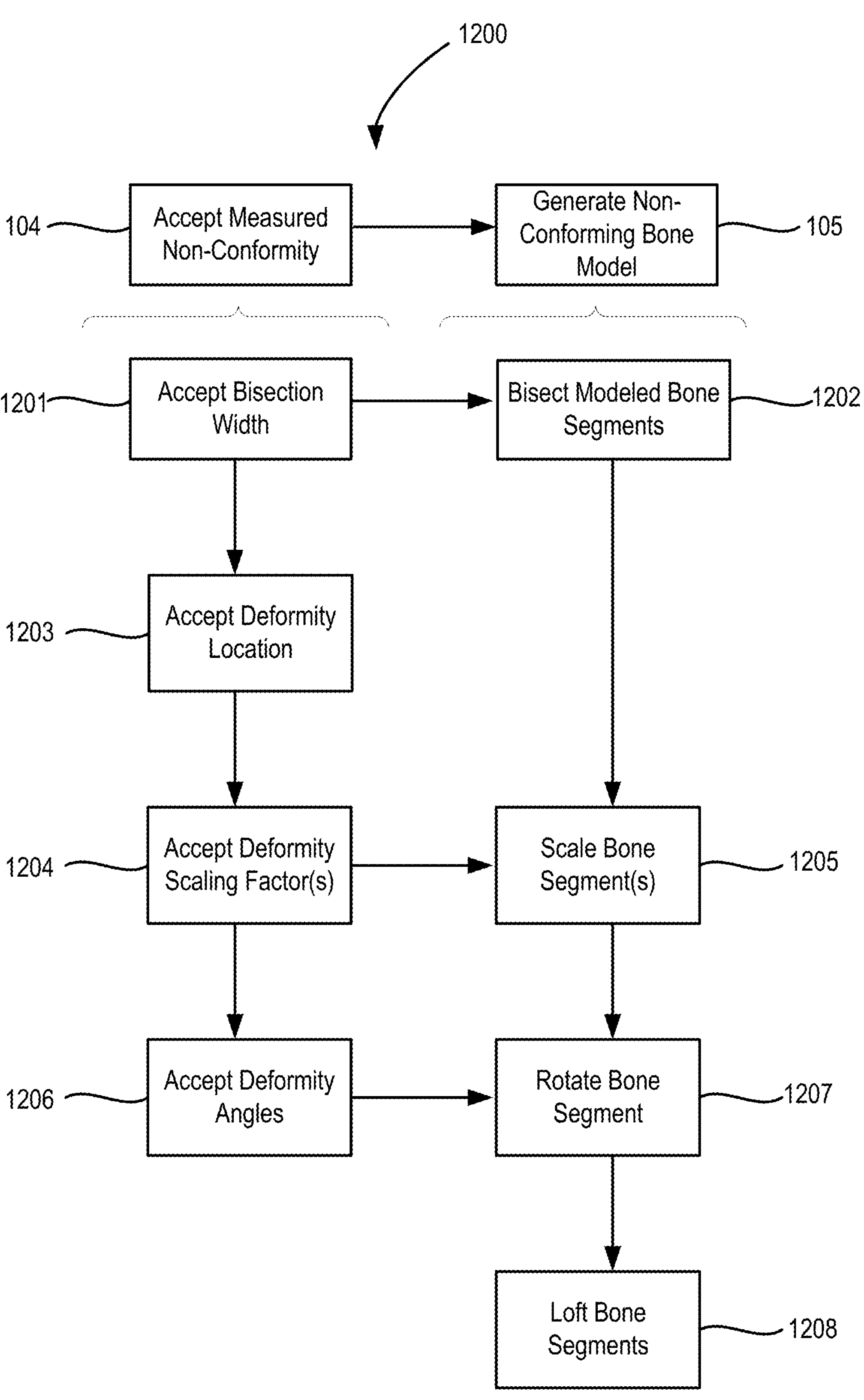
FIG. 12 illustrates a flow chart for a set of methods for accepting a measured nonconformity and generating a nonconforming bone model based thereon in accordance with specific embodiments of the inventions disclosed herein.

FIG. 12 illustrates a flow chart 1200 for a set of methods for accepting a measured nonconformity and generating a nonconforming bone model. Flow chart 1200 begins with step 1201 of accepting a bisection width. The width can be entered into a user interface element in the design environment in similar fashion to how the variables discussed above were entered. The bisection width can be selected based on the nonconformity that will be modeled for a given nonconforming bone model. For example, larger bisection widths are better for large deformities while smaller cut depths are better for sudden and acute deformities. The distance of the deformity will be greater than half the bisection width to avoid bisecting at the joint or bisecting one half of the bone away completely.

Figure 13:
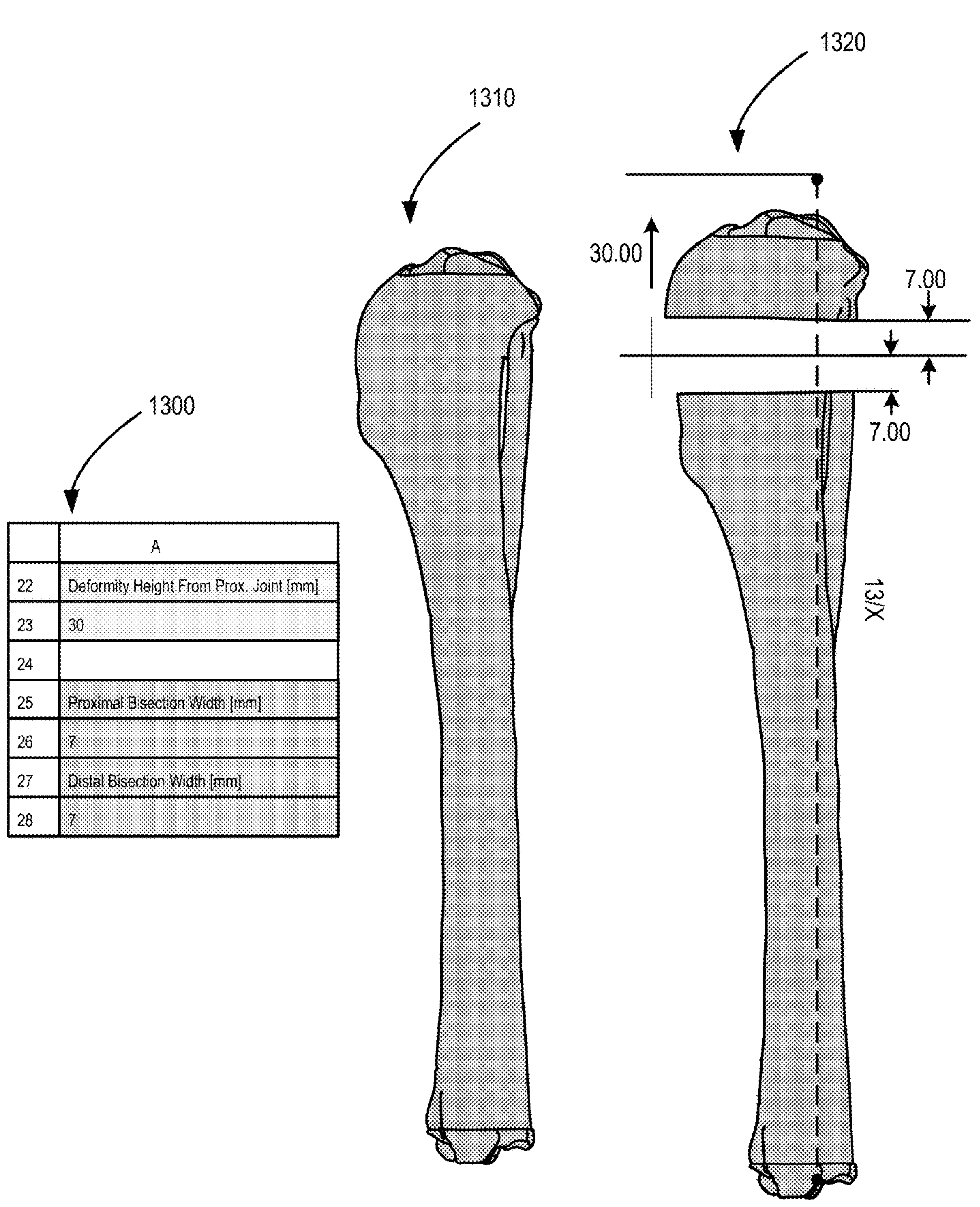
FIG. 13 illustrates a user interface for accepting a bisection width in accordance with specific embodiments of the inventions disclosed herein.

FIG. 13 illustrates a user interface 1300 for entering a bisection width which in the illustrated case can be provided in two pieces—one for the proximal bisection width and one for the distal bisection width. The conforming bone model 1310 and resulting bisected bone model 1320 are also illustrated in FIG. 13. The bisected bone model 1320 results from the execution of step 1202 in which the conforming bone model is bisected into two separate bone segments. Step 1202 can involve separating a first modeled bone segment from a second modeled bone segment by the bisection width. Step 1202 can also be conducted on a scaled bone model. Once the two separate bone segments have been formed, they can be individually treated by the model. Also, as can be seen in the figure since, the conforming bone template models 1310 is defined by a singular closed surface extending through where the bisected distance has been selected. The singular closed surface provides a singular perimeter for the ends of both bone segments which can be easily modeled and treated as a closed surface in the model of the two bone segments.

Figure 14:
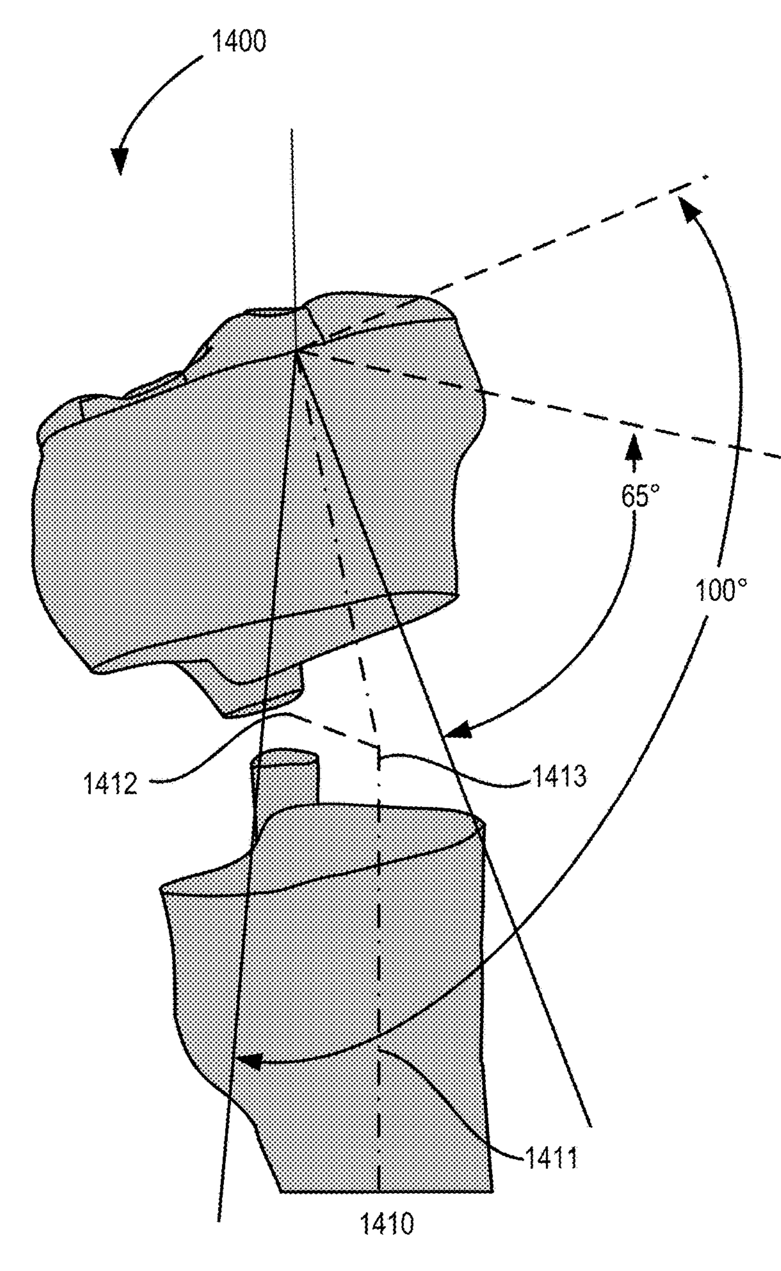
FIG. 14 illustrates a user interface for accepting a nonconformity angle in accordance with specific embodiments of the inventions disclosed herein.

Flow chart 1200 continues with a step 1203 of accepting a deformity location and a step 1206 of accepting a deformity angle. In specific embodiments, the location of the deformity can be presumed to be centered on the coronal plane cross section of the bone segments and at the center of the bisection width. However, in alternative embodiments, the location of the deformity can be defined as offset from this point. The angle of the deformity can then be defined in the sagittal and frontal planes similarly to the approach described above with reference to FIG. 5. In the illustrated case of FIG. 14, the deformity angles are provided in the form of a sagittal angle and frontal angle provided in a user interface 1400 and as represented by bone model 1410. Flow chart 1200 can then continue with step 1207 of rotating the bone segments according to the defined deformity angle. The step can involve rotating the first modeled bone segment at the deformity location by the deformity angle after separating the first modeled bone segment from the second modeled bone segment.

The deformity angles can be defined in various ways. The angles can be a direct input to a feature tree output of the model of the bisected bone segments. The angles in the frontal and sagittal planes can completely define a three-dimensional vector of the deformity. In specific embodiments, such as those in accordance with FIG. 14, a deformity in the distal joint can point to a proximal deformity vector at the deformity distance. As such, there is no requirement for a second deformity input for the distal joint. In these embodiments, two orthogonal three-dimensional vectors (one in the sagittal plane 1411, and one in the frontal plane 1412) meet at the deformity distance 1413 using only the joint deformities provided with respect to one joint. The rendered bone will automatically adjust to any new deformity values input into interface 1400 and the operator does not need to input opposite joint deformities. In alternative embodiments, the model can allow a user to describe the deformity with respect to its distal qualities.

In specific embodiments, the segmented bone segments can be scaled about coordinate systems while bisected to increase fidelity of the nonconforming bone model to the patient bone. This concept is represented in flow chart 1200 by step 1204 of accepting deformity scaling factors from an operator and step 1205 of scaling the bone segments accordingly. The individual bone segments can be scaled independently in specific embodiments which is advantageous in that the two joint interfaces of the bone will be on different segments and may not, due to certain deformities, scale equally with parameters such as the length of the bone. While the bone model is bisected into two separate solid bodies, each can be scaled in their own coordinate system according to their three-dimensional deformation scalars, so that their lengths do not change at all, but their critical frontal and sagittal widths at crucial locations in each joint can be made to match the patient very closely. FIG. 15 includes a rendering of a conformal bone model 1500, a scaled bisected proximate bone segment 1501, and a user interface 1502 that can be used to enter the scaling factors. As illustrated the scaling factors are specific to the "Prox." or proximal bone segment. Different inputs can be utilized to separately define scaling factors for the distal bone segment. At 100 mm scale, widths are recorded for both perspectives at each joint, according to carefully located markers. When scaled to patient length by scalar, initial measured widths increase or decrease by the same amount. Since scaled joint dimensions can be calculated, the scalar needed to scale to a specific size can be calculated by dividing the desired size by the actual size after the primary scaling from 100 mm stock bone. The joint can be scaled in one axis at a time so that each desired dimension can be reached without skewing any other values.

In specific embodiments, the bone segments can be rotated while bisected. While the bone is bisected into two separate solid bodies, the proximal and distal end can be coronally rotated to more accurately model a certain bone deformity. FIG. 16 includes a custom SolidWorks API 1600 that can be used with a custom visual basic (VB) macro 1620 to convert inputs that define a desired degree of rotation in a user input 1610 to produce the rotation of the model shown in view 1630. The unshaded tibia displayed in view 1630 is a pure coronal rotation of the shaded tibia bone. For SolidWorks 2023, there is no easily available rotation adjustment for the excel sheet syntax, so the custom Visual Basic (VB) code and SolidWorks API are used to copy custom values from the spreadsheet to a simple sketch line length. That Sketch line has its value copied to a rotation value in a feature, to get the same effect. A stock rotation amount for zero coronal adjustment is 360 degrees, so the operator can input negative rotation, and get the intended result, but the CAD program never has issues crossing the 0-point reference frame. Because VB code uses the typical spreadsheet design table to insert the rotation amount to a sketch, all inputs are still made in the same place, and the user can use a simple macro button to update their model in a more complex way than SolidWorks would allow by default.

Flow chart 1200 continues with a step 1208 of lofting the first modeled bone segment to the second modeled bone segment after rotating the first modeled bone segment in step 1207. This process is illustrated in FIG. 17 which shows a view of the separated bone segments 1700 after they have been rotated to model the deformity and a view of the bone segments after they have been lofted together 1710. As shown, the segments are joined by segments 1711 and 1712 which have been added to rejoin the bone segments and complete the generation of the nonconforming bone model. Now that each half of the bone has been scaled and manipulated separately, they can be lofted back together as a more accurate representation of the patient bone than would have been possible to make if the bone has been manipulated as one piece. By manipulating the model in a deliberate order, it is possible to achieve very specific results with fundamental and non-complex operations that are reliable and robust. Since the column of the bone is one surface, any cut of that surface will result in a continuous homogenous perimeter at every cut surface. This one perimeter is what is selected for the loft. This way the loft reforms automatically without any user input regardless of the deformity values, cut depths, or deformity distance.

In specific embodiments of the inventions, the nonconformity can be a nonconforming surface of a bone such that accepting a nonconformity of the patient bone as in step 102 comprises accepting values that define a cortical surface of interest. The cortical surface can be defined with reference to specific planes and angles that define the nonconformity of the cortical surface relative to a corresponding conformal cortical surface. In specific embodiments, the measured nonconformity is accepted in the form of a set of numbers. The set of numbers can be defined using various user interface elements. Regardless of the manner in which they are accepted, the numbers can be a set of numbers that are easily obtained using standard procedures for measuring the characteristics of a given bone. In specific embodiments, the numbers can be obtained using standard two-dimensional radiographs or derived values that are obtained from a three-dimensional scan of a patient's limb. The set of numbers can include specific angles that define the cortical surface of interest relative to one or more bone planes the bisect the surface of interest. While the example of a medial tibial cortex if provided in the following discussion, the approach is more broadly applicable to the generation of bone models having any type of nonconforming cortical surface.

A method for generating a nonconformal bone model in which the nonconformity is a nonconforming cortical surface can begin with a step of defining bone planes and an angulation of the cortical surface of interest relative to those planes. The angulation can be accepted from an operator with respect to specific bone planes. In specific embodiments, the process can also include creating cross sectional surface profiles of a conformal bone template or scaled conformal bone template at those planes, measuring an offset between the surface profiles and the surface profiles that would result from the accepted angulation, and generating a scale factor for scaling the bone model based on those offsets. The nonconformal bone model can then be generated from the scaled, translated and rotated surface profiles in a lofting operation.

The set of numbers that are accepted in order to define a nonconforming cortical surface depend on the bone and bone segment in question. Generally, the nonconforming cortical surface can be defined based on various typical values used to describe anatomical structures in a patient's bones or joints. For example, the set of numbers that are accepted in order to define a nonconformity of a medial tibial cortex are as follows and can be described with reference to FIG. 18. The figure includes a sagittal view 1800 showing three planes in which the angulation of the nonconformal surface will be defined, a frontal view 1810 to illustrate two values for defining the nonconformity, and a transverse view 1820 along with a set of transverse views 1830 showing the transverse view cross section of the bone at each of the three planes marked in view 1800. The set of numbers can include a proximal distal medial tibial cortex flare angle (PD mTC-flare) and a proximal distal medial tibial cortex diaphysis (PD mTC-d) as labeled in view 1810. The values can also include the sagittal width of the proximal tibia. As can be seen, measurements for the entirety of the bone column are not necessary, as the mechanical axis (MA) length may be defined without it. Therefore, in the context of modeling a cortical surface of a proximal distal medial tibial cortex, the conformal bone model only needs to be able to generate the proximal half of the medial tibial cortex and maintain the angular relation of that generated surface to the bone planes. The nonconformity can be defined with variables in the medial tibial cortex (mTC) angulation column, since those impact the trajectory of the simulated action relative to the bone planes. The labels in FIG. 18 include proximodistal (PD), craniocaudal (CC), mechanical caudal proximal tibial angle (mCdPTA), mechanical medial proximal tibial angle (mMPTA), mechanical cranial distal tibial angle (mCrDTA), mechanical medial distal tibial angle (mMDTA), and the tibial plateau angle (TPA) which is equal to 90 degrees minus the mCdPTA. As illustrated, the CC mTC angulation is measured as the angular intersection of the slope of the medial tibial cortex with respect to the sagittal plane as observed in the coronal plane, while the PD mTC angulation is measured as the angular intersection of the slope of the medial tibial cortex with respect to the sagittal plane as observed in the frontal plane. The mTC flare is the additional angular magnitude observed in the frontal plane at the junction of the proximal tibial condyle. The best fit circle typifies the proximal tibial condyle and may be utilized for development of conformal implants and guides, as well as determining the site of the medial tibial cortex at this coronal section that the mTC-Op may be calculated. In specific embodiments, the set of values for defining the nonconformity include the three angles in view 1830 and the two values in view 1810.

The following table provides values for the various parameters that can be altered to produce a scaled conforming bone template model or to specify the nonconformities associated with a nonconforming proximal medial tibia.

| BONE LINEAR DIMENSIONS (mm) | JOINT ORIENTATION ANGLES (deg.) | mTC ANGULATION (deg.) |
|---|---|---|
| MA: 170.2 | mCdPTA: 60 | CC mTC-Dd: 15 |
| Proximal Frontal Width: 39.3 | mMPTA: 93 | CC mTC-Dp: 25 |
| Proximal Sagittal Width: 39.7 | mCrDTA: 84 | CC mTC-Op: 30 |
| Distal Frontal Width: 18.5 | mMDTA: 95 | PD mTC-diaphyseal angle: 3 |
| Distal Sagittal Width: 23.7 | Torsion introduced: 0 | Frontal plane (mTC flare) 25 |

FIG. 19 illustrates an approach for calculating the offsets required to generate a nonconforming bone model with a nonconforming medial tibial cortex in accordance with specific embodiments of the inventions disclosed herein. As mentioned previously, a method for generating a nonconformal bone model in which the nonconformity is a nonconforming cortical surface can include creating cross sectional surface profiles of a conformal bone template or scaled conformal bone template at those planes, measuring an offset between the surface profiles and the surface profiles that would result from the accepted angulation, and generating a scale factor for scaling the bone model based on those offsets. FIG. 19 shows a frontal view 1900 in which a set of offsets at three planes of interest have been calculated and an axonometric view 1910 that relates those offsets to angulations entered at those planes.

Figure 20:
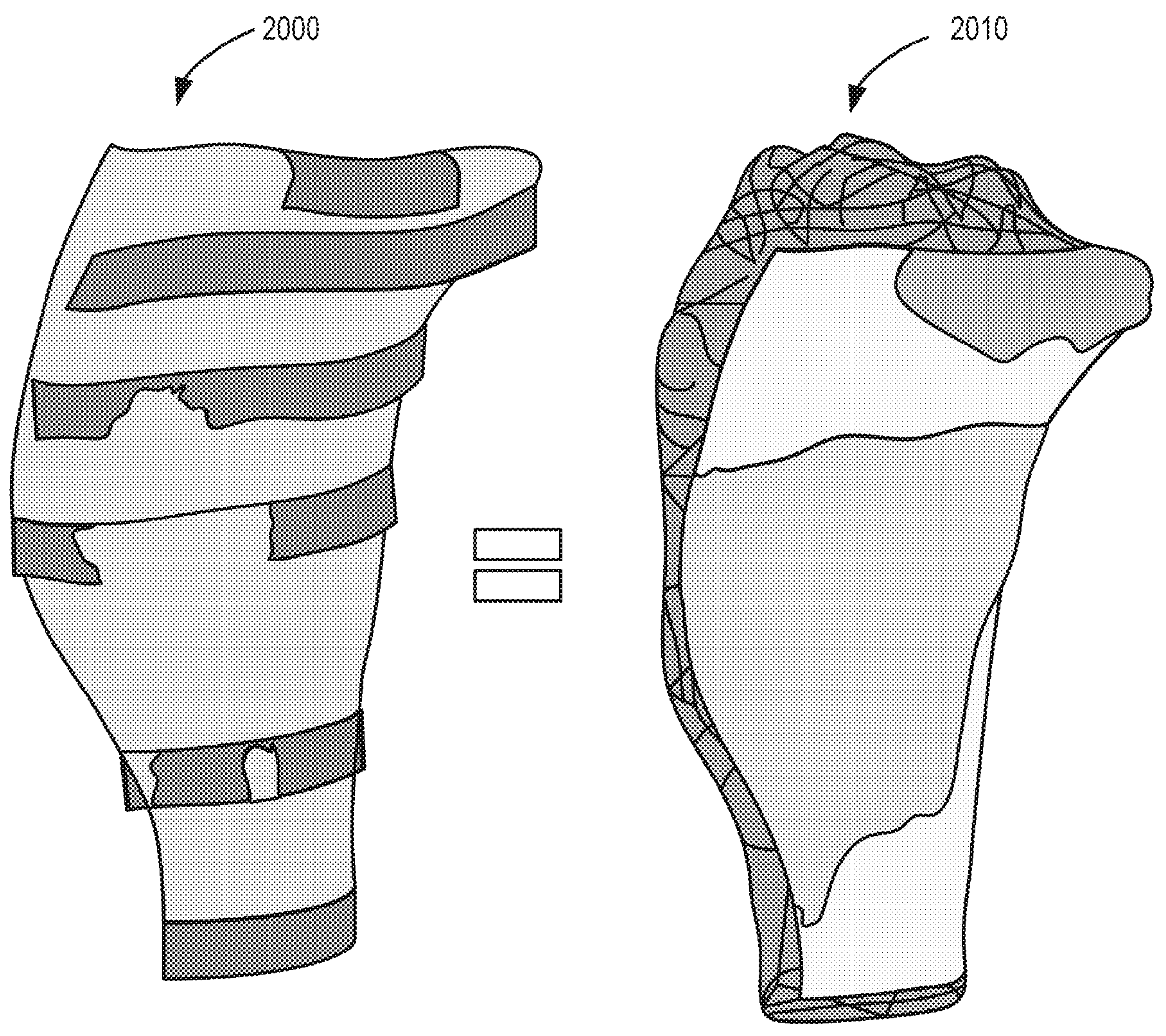
FIG. 20 illustrates a nonconforming bone model with a nonconforming medial tibial cortex in accordance with specific embodiments of the inventions disclosed herein.

FIG. 20 illustrates a nonconforming bone model with a nonconforming medial tibial cortex in accordance with specific embodiments of the inventions disclosed herein. The offsets and scale factors calculated in the process illustrated by FIG. 19 can be used to determine scaled surface profiles as illustrated by the strips off the main cortical surface in view 1900 and view 1910. More of these surface profiles are shown in view 2000 in FIG. 20. The nonconformal bone model with its nonconformal surface can then be generated from the scaled, translated and rotated surface profiles and a lofting operation to join strips that are formed by the surface profiles. The final nonconformal surface is shown in view 2010 in which the nonconformal surface is overlain on the underlying conformal bone model surface.

In specific embodiments of the invention, the generated nonconforming bone model can be used and interacted with in various ways (e.g., to perform an osteotomy, create a drill guide, create a pin guide, make an implant, alter conformation or alignment, etc.). In specific embodiments of the invention in which the bone model is being used to correct a nonconformity, once the conformation of the bone has been fully described, the proposed corrective osteotomy could be planned using the model. The system can use anatomic landmarks, fiducial markers and/or topographic triangulation to spatially constrain the implant(s) and CAD component modeling functions relative to the CAD bone rendering. In specific embodiments the system can be used to generate patient specific and/or anatomic specific implants, cut guides, or other surgical implements using the nonconforming bone model (e.g., a nonconforming bone surface used to produce an anatomic patient specific surgical implement). The system can produce such surgical implements with or without CT imaging as the nonconforming bone models can be produced with or without CT imaging using the approaches disclosed herein. In specific embodiments of the invention, the system will be able to automatically generate patient-specific surgical equipment such as cutting guides or implants based on the CAD model of the bone. In specific embodiments of the invention, the process can terminate with the generation of a post operative bone model which models the state of a bone after a surgery has been performed as the bone has been effectively modeled through to the end of the procedure.

In the context of using models for corrective osteotomy or osteotomies, once a representative three-dimensional model of the deformity has been generated, whether it be a mesh or CAD file, the corrective osteotomy or osteotomies can be planned. Using the approaches disclosed herein, the process of obtaining the model can be objectified while using CAD by removing the conventional requirements for manual deformity calculations and cross-referencing CORA locations between CT and MPR images to the mesh file. Instead, the operator can provide the measured magnitude of deformity obtained from each orthogonal plane in addition to the location of any CORAs, and the true plane of deformity and its magnitude can be automatically calculated. Osteotomies can then be planned in a manner that is more time efficient, with minimal user involvement and potentially reduced human error risk.

Figure 21:
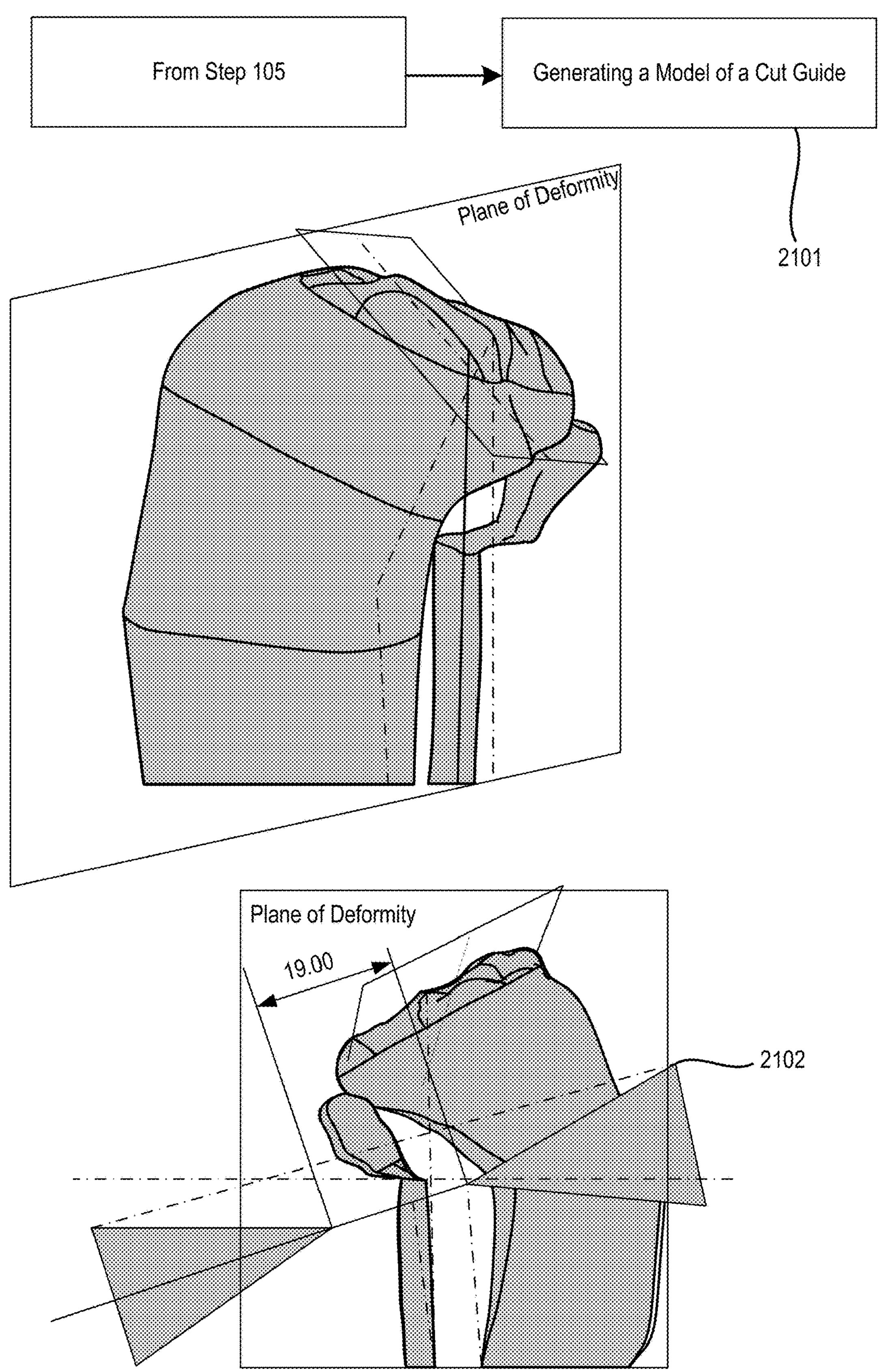
FIG. 21 illustrates a flow chart for generating a model of a cut guide in accordance with specific embodiments of the inventions disclosed herein.

FIG. 21 includes a flow chart for generating a model of a patient-specific surgical element in the form of a cut guide. As illustrated, the process can continue from step 105 of flow chart 100 and continue with step 2101 of generating a model of the cut guide using the nonconforming bone model and a set of cut lines. The set of cut lines can be automatically generated based on the measured nonconformity. For example, the cut lines can be set by the perimeters of the two surfaces of the bisected bone segments that are lofted together in step 1208. The process can also include a step of displaying a sketch of an appropriate region for the cut guide and cuts 2102 on the nonconforming bone model. The process can also include a step illustrated in FIG. 22 of displaying a model of the cut guide 2200 on the bone. The process can also include a step illustrated in FIG. 22 of displaying a post operative bone model 2210 of the patient bone based on the model of the cut guide and the nonconforming bone model.

In specific embodiments, the plane of deformity can be derived from using two deformity vectors which can be derived from two angles used to define the nonconformity when the nonconformity is first input by the operator and accepted by the design environment. These two vectors can be used to define a plane which is the plane of the deformity. A straight cut made on this plane can allow the bone halves to join evenly if a special cut is made. Setting the model of the cut guide's edges to be parallel with existing cut-lines in the model creates the exact wedge cut geometry to be removed for proper deformity correction. The wedge being cut can be automatically generated by the system so that it is overly long (i.e., the plane of the deformity can be made to extend just beyond the confine of the bone). This is possible because a proper cut in the illustrated situations only requires that the wedge begin as close as possible to the edge of the bone on the acute side of the deformity. The wedge's offset from the center at which it cuts affects the gap in the corrected bone to be larger or smaller. Mirroring the cut across the center means the feature works for all deformities, even mirrored ones. Accordingly, the automatically generated cut guide will not often need to be adjusted by the operator.

When the axes that were used to define the deformity in the bone are returned to the ideal axis of the original bone template, the cut can be seen to have made parallel surfaces, ready to be compressed and stabilized. The original gap distance is the volume of bone removed via the osteotomy (ies). The specific guide shown is for a closing wedge osteotomy. However, the system can be used to generate guides for other types of osteotomies. This example covers the default wedge style cut. But this modeled patient-specific surgical element can be swapped out with other cut styles to cover any other osteotomy processes such as a modified closing wedge, opening wedge, dome osteotomies, radial osteotomies, etc.

An example of a nonconforming bone model being generated and used to automatically plan a surgery involving patient-specific surgical equipment that is automatically designed using the approaches disclosed herein can be explained as follows. The nonconformity used in many of the examples herein is a bone deformity and the surgery involves an osteotomy and translation of the bone. However, as mentioned previously, the approaches disclosed herein are more broadly applicable to the generation of bone models for any nonconforming bone and for supporting and planning multiple different kinds of surgeries.

While the specification has been described in detail with respect to specific embodiments of the invention, it will be appreciated that those skilled in the art, upon attaining an understanding of the foregoing, may readily conceive of alterations to, variations of, and equivalents to these embodiments. Any of the method steps discussed above can be conducted by a processor operating with a computer-readable non-transitory medium storing instructions for those method steps. The computer-readable medium may be memory within a personal user device or a network accessible memory. Although examples in the disclosure where generally directed to bone model generation for supporting surgeries, the bone models generated using the approaches disclosed herein could be applied to numerous other applications such as for product prototyping, educational purposes, and other applications. These and other modifications and variations to the present invention may be practiced by those skilled in the art, without departing from the scope of the present invention, which is more particularly set forth in the appended claims.

What is claimed is:

1. A method for generating a bone model for a patient bone, in which each step is computer-implemented, comprising:

storing a conforming bone template model;

accepting a nonconformity of the patient bone, wherein:

the nonconformity is accepted as a set of numbers; and the set of numbers includes a proximal distal medial tibial cortex flare angle and a proximal distal medial tibial cortex diaphysis;

generating a nonconforming bone model using the nonconformity of the patient bone and the conforming bone template model;

wherein the nonconformity is used to set a constraint of the conforming bone template model to a value and the nonconforming bone model has the value for the constraint.

2. The method of claim 1, further comprising:

accepting a selection of a bone type; and displaying, prior to accepting the nonconformity and after accepting the selection of the bone type, the conforming bone template model of the bone type.

3. The method of claim 1, further comprising:

accepting a scaling factor; and scaling the conforming bone template model by the scaling factor to produce a scaled conforming bone template model.

4. The method of claim 3, further comprising:

displaying, prior to accepting the nonconformity and after accepting the scaling factor, the scaled conforming bone template model.

5. The method of claim 3, wherein:

the scaling factor is one of a frontal scaling factor and a sagittal scaling factor.

6. The method of claim 3, wherein:

the scaling factor is a desired length of the patient bone.

7. The method of claim 1, further comprising:

displaying the nonconforming bone model; and iteratively: (i) accepting a revised measured nonconformity of the patient bone; (ii) generating a revised nonconforming bone model using the revised measured nonconformity; and (iii) displaying the revised nonconforming bone model.

8. The method of claim 1, wherein:

the nonconformity is accepted as a set of numbers that are one of: (i) entered into input fields; (ii) selected on a selection interface.

9. The method of claim 1, wherein:

the nonconformity is accepted as a set of numbers; and the set of numbers includes a distance of the nonconformity from a joint of the patient bone.

10. The method of claim 1, wherein:

the nonconformity is accepted as a plane of the nonconformity and a magnitude of the nonconformity.

11. The method of claim 1, wherein:

the constraint of the conforming bone template model is a distance from a joint to a plane of the nonconformity;

the nonconformity is used to set a second constraint of the conforming bone template model to a second value and the nonconforming bone model has the second value for the second constraint;

the nonconformity is used to set a third constraint of the conforming bone template model to a third value and the nonconforming bone model has the third value for the third constraint;

the second constraint of the conforming bone template model is a magnitude of the nonconformity expressed as an angle in the sagittal plane; and the third constraint of the conforming bone template model is a magnitude of the nonconformity expressed as an angle in the frontal plane.

12. The method of claim 1, wherein accepting the nonconformity of the patient bone further comprises:

accepting a bisection width; and accepting a deformity angle.

13. The method of claim 12, wherein generating the nonconforming bone model further comprises:

separating a first modeled bone segment from a second modeled bone segment by the bisection width;

rotating the first modeled bone segment by the deformity angle after separating the first modeled bone segment from the second modeled bone segment; and lofting the first modeled bone segment to the second modeled bone segment after rotating the first modeled bone segment.

14. The method of claim 12, further comprising:

separating a first modeled bone segment from a second modeled bone segment by the bisection width;

accepting a scaling factor for the first modeled bone segment; and scaling the first modeled bone segment independently of the second modeled bone segment using the scaling factor.

15. The method of claim 1, wherein:

the nonconformity is a nonconforming surface of the patient bone.

16. A method for generating a cut guide for an osteotomy on a patient bone, in which each step is computer-implemented, comprising:

storing a conforming bone template model;

accepting a measured nonconformity of the patient bone; wherein accepting the measured nonconformity of the patient bone further comprises: (i) accepting a bisection width; (ii) accepting a deformity location; and (iii) accepting a deformity angle;

generating a nonconforming bone model using the measured nonconformity and the conforming bone template model, wherein the nonconforming bone model includes cut lines automatically generated based on the measured nonconformity; and generating a model of the cut guide using the nonconforming bone model and the cut lines.

17. The method of claim 16, further comprising:

displaying the model of the cut guide on the nonconforming bone model; and displaying a post operative bone model of the patient bone based on the model of the cut guide and the nonconforming bone model.

18. A method for generating a bone model for a patient bone, in which each step is computer-implemented, comprising:

storing a conforming bone template model;

accepting a scaling factor;

scaling the conforming bone template model by the scaling factor to produce a scaled conforming bone template model;

displaying the scaled conforming bone template model;

accepting a nonconformity of the patient bone; and generating a nonconforming bone model using the nonconformity of the patient bone and the conforming bone template model;

wherein the nonconformity is used to set a constraint of the conforming bone template model to a value and the nonconforming bone model has the value for the constraint.

19. A method for generating a bone model for a patient bone, in which each step is computer-implemented, comprising:

storing a conforming bone template model;

accepting a nonconformity of the patient bone; and generating a nonconforming bone model using the nonconformity of the patient bone and the conforming bone template model;

wherein the nonconformity is used to set a constraint of the conforming bone template model to a value and the nonconforming bone model has the value for the constraint, wherein:

the constraint of the conforming bone template model is a distance from a joint to a plane of the nonconformity;

the nonconformity is used to set a second constraint of the conforming bone template model to a second value and the nonconforming bone model has the second value for the second constraint;

the nonconformity is used to set a third constraint of the conforming bone template model to a third value and the nonconforming bone model has the third value for the third constraint;

the second constraint of the conforming bone template model is a magnitude of the nonconformity expressed as an angle in the sagittal plane; and the third constraint of the conforming bone template model is a magnitude of the nonconformity expressed as an angle in the frontal plane.

20. A method for generating a bone model for a patient bone, in which each step is computer-implemented, comprising:

storing a conforming bone template model;

accepting a nonconformity of the patient bone;

generating a nonconforming bone model using the nonconformity of the patient bone and the conforming bone template model;

wherein the nonconformity is used to set a constraint of the conforming bone template model to a value and the nonconforming bone model has the value for the constraint;

accepting a bisection width;

accepting a deformity angle;

separating a first modeled bone segment from a second modeled bone segment by the bisection width;

rotating the first modeled bone segment by the deformity angle after separating the first modeled bone segment from the second modeled bone segment; and lofting the first modeled bone segment to the second modeled bone segment after rotating the first modeled bone segment.

21. A method for generating a bone model for a patient bone, in which each step is computer-implemented, comprising:

storing a conforming bone template model;

accepting a nonconformity of the patient bone;

generating a nonconforming bone model using the nonconformity of the patient bone and the conforming bone template model;

wherein the nonconformity is used to set a constraint of the conforming bone template model to a value and the nonconforming bone model has the value for the constraint;

accepting a bisection width;

accepting a deformity angle;

separating a first modeled bone segment from a second modeled bone segment by the bisection width;

accepting a scaling factor for the first modeled bone segment; and scaling the first modeled bone segment independently of the second modeled bone segment using the scaling factor.

* * * * *